US012270041B2

(12) United States Patent (10) Patent No.: US 12,270,041 B2
Yalovsky et al. (45) Date of Patent: Apr. 8, 2025

(54) ROP—DEFICIENT PLANTS HAVING HIGH WATER USE EFFICIENCY

(71) Applicant: RAMOT AT TEL-AVIV UNIVERSITY LTD., Tel Aviv (IL)

(72) Inventors: Shaul Yalovsky, Tel Aviv (IL); Malikarjuna Rao Puli, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 324 days.

(21) Appl. No.: 17/779,355

(22) PCT Filed: Nov. 25, 2020

(86) PCT No.: PCT/IL2020/051212
§ 371 (c)(1),
(2) Date: May 24, 2022

(87) PCT Pub. No.: WO2021/105986
PCT Pub. Date: Jun. 3, 2021

(65) Prior Publication Data
US 2023/0026620 A1 Jan. 26, 2023

Related U.S. Application Data

(60) Provisional application No. 63/008,754, filed on Apr. 12, 2020, provisional application No. 62/940,265, filed on Nov. 26, 2019.

(51) Int. Cl.
*C12N 15/82* (2006.01)
*C07K 14/415* (2006.01)
(52) U.S. Cl.
CPC ........ *C12N 15/8273* (2013.01); *C07K 14/415* (2013.01); *C12N 15/8213* (2013.01)
(58) Field of Classification Search
None
See application file for complete search history.

(56) References Cited

U.S. PATENT DOCUMENTS

| | | | |
|---|---|---|---|
| 2004/0006783 | A1 | 1/2004 | Yang |
| 2006/0137042 | A1 | 6/2006 | Plesch |
| 2009/0044291 | A1 | 2/2009 | Zhang |
| 2015/0007364 | A1 | 1/2015 | Maor |

FOREIGN PATENT DOCUMENTS

| | | |
|---|---|---|
| CN | 102731639 A | 10/2012 |
| WO | 2009/027539 A2 | 3/2009 |
| WO | 2009104181 A1 | 8/2009 |

OTHER PUBLICATIONS

Feiguelman et al, 2018, Plant Physiology 176: 57-79 (Year: 2018).*
Li et al, 2012, FEBS Letters 586: 1253-1258 (Year: 2012).*
Puli et al, Jul. 2018, ISRR-10 Conference Presentation Abstract, "Tomato Root Development: Characterizing the Potential Role of Tomato ROP-GTPases SIROP4 and SIROP9" (Year: 2018).*
UniProt Accession K4BKQ9_SOLLC, Mar. 28, 2018; https://www.uniprot.org/uniprotkb/K4BKQ9/history. (Year: 2018).*
Zhang et al, 2011, Biotechnology Letters 33: 403-409. (Year: 2011).*
Belhaj et al., (2013) Plant genome editing made easy: targeted mutagenesis in model and crop plants using the CRISPR/Cas system. Plant Methods 9(1):39.
Bloch et al., (2011) Nitrogen source interacts with ROP signalling in root hair tip-growth. Plant Cell Environ 34(1): 76-88.
Bloch et al., (2019) Abiotic stress modulates root patterning via ABA-regulated microRNA expression in the endodermis initials. Development 146(17): dev177097.
Bracha-Drori et al., (2004) Detection of protein-protein interactions in plants using bimolecular fluorescence complementation. Plant J 40(3): 419-427.
Choi et al., (2014) *Arabidopsis* ROP9 and ROP10 GTPases differentially regulate auxin and ABA responses. Journal of Plant Biology 57: 245-254.
Clough and Bent (1998) Floral dip: a simplified method for Agrobacterium-mediated transformation of *Arabidopsis thaliana*. Plant J 16(6): 735-743.
Dalal et al., (2019) Dynamic Physiological Phenotyping of Drought-Stressed Pepper Plants Treated With "Productivity-Enhancing" and "Survivability-Enhancing" Biostimulants. Front Plant Sci 10: 905.
Dalal et al., (2020) A High-Throughput Gravimetric Phenotyping Platform for Real-Time Physiological Screening of Plant-Environment Dynamic Responses. bioRxiv DOI: 10.1101/2020.01.30.927517; PPR: PPR111135.
Duan et al., (2014) Reactive oxygen species mediate pollen tube rupture to release sperm for fertilization in *Arabidopsis*. Nat Commun 5: 3129.
Duan et al., (2010) Feronia receptor-like kinase regulates RHO GTPase signaling of root hair development. Proc Natl Acad Sci U S A 107(41): 17821-17826.
Feiguelman et al., (2018) ROP GTPases Structure-Function and Signaling Pathways. Plant Physiol 176(1): 57-79.
Gaj et al., (2013) ZFN, Talen, and CRISPR/Cas-based methods for genome engineering. Trends Biotechnol 31(7): 397-405.
Gao et al., (2016) ABF2, ABF3, and ABF4 Promote ABA-Mediated Chlorophyll Degradation and Leaf Senescence by Transcriptional Activation of Chlorophyll Catabolic Genes and Senescence-Associated Genes in *Arabidopsis*. Mol Plant 9(9): 1272-1285.
Halperin et al., (2017) High-throughput physiological phenotyping and screening system for the characterization of plant-environment interactions. Plant J 89(4): 839-850.
Hatfield and Dold (2019) Water-Use Efficiency: Advances and Challenges in a Changing Climate. Front Plant Sci 10: 103.
Henikoff and Henikoff (1992) Amino acid substitution matrices from protein blocks. Proc Natl Acad Sci U S A 89(22): 10915-10919.

(Continued)

*Primary Examiner* — Brent T Page
*Assistant Examiner* — Alesandar Radosavljevic
(74) *Attorney, Agent, or Firm* — Dorsey & Whitney LLP

(57) ABSTRACT

The present invention relates to plants, particularly to crop plants including plants of the family Solanaceae having reduced expression and/or activity of Sl ROP9 protein or homologs thereof, displaying increased water use efficiency (WUE) and enhanced tolerance to drought and/or salt stress, with minimal effect on the crop yield.

20 Claims, 22 Drawing Sheets

Specification includes a Sequence Listing.

(56) References Cited

OTHER PUBLICATIONS

Hopes et al., (2017) Genome Editing in Diatoms Using CRISPR-Cas to Induce Precise Bi-allelic Deletions. Bio Protoc 7(23): e2625.
Lavy et al., (2007) A Novel ROP/RAC effector links cell polarity, root-meristem maintenance, and vesicle trafficking. Curr Biol 17(11): 947-952.
Lemichez et al., (2001) Inactivation of AtRac1 by abscisic acid is essential for stomatal closure. Genes Dev 15(14): 1808-1816.
Li et al., (2012) ROP11 GTPase negatively regulates ABA signaling by protecting ABI1 phosphatase activity from inhibition by the ABA receptor RCAR1/PYL9 in *Arabidopsis*. J Integr Plant Biol. Author manuscript; available in PMC Mar. 4, 2013. Published in final edited form as: J Integr Plant Biol. Mar. 2012; 54(3): 180-188.
Li and Liu (2012) ROPGEF1 and ROPGEF4 are functional regulators of ROP11 GTPase in ABA-mediated stomatal closure in *Arabidopsis*. FEBS Lett 586(9): 1253-1258.
Li et al., (2012) ROP11 GTPase is a negative regulator of multiple ABA responses in *Arabidopsis*. J Integr Plant Biol 54(3): 169-179.
McCormick et al., (1986) Leaf disc transformation of cultivated tomato (L. esculentum) using Agrobacterium tumefaciens. Plant Cell Rep 5(2): 81-84.
Merlot et al., (2002) Use of infrared thermal imaging to isolate *Arabidopsis* mutants defective in stomatal regulation. Plant J 30(5): 601-609.
Nir et al., (2017) The Tomato Della Protein Procera Acts in Guard Cells to Promote Stomatal Closure. Plant Cell 29(12): 3186-3197.
Potrykus (1991) Gene Transfer to Plants: Assessment of Published Approaches and Results. Annu Rev Plant Physiol Plant Mol Biol 42: 205-225.
Puli and Raghavendra (2012) Pyrabactin, an ABA agonist, induced stomatal closure and changes in signalling components of guard cells in abaxial epidermis of Pisum sativum. J Exp Bot 63(3): 1349-1356.
Puli and Yalovsky (2018) Tomato Root Development: Characterizing the Potential Role of Tomato ROPGTPases SlROP4 and SlROP9. Presented at the ISRR-10, Exposing the Hidden Half. Root Research at the Forefront of Science International Symposium. Jul. 8-12, 2018, Yearim Hotel, Israel. Abstract.
Shimamoto et al., (1989) Fertile transgenic rice plants regenerated from transformed protoplasts. Nature 338: 274-276.
Siligato et al., (2016) MultiSite Gateway-Compatible Cell Type-Specific Gene-Inducible System for Plants. Plant Physiol 170(2): 627-641.
Wong et al., (2007) Regulation of rice NADPH oxidase by binding of Rac GTPase to its N-terminal extension. Plant Cell 19(12): 4022-4034.
Xin et al., (2005) Transcriptome analysis reveals specific modulation of abscisic acid signaling by ROP10 small GTPase in *Arabidopsis*. Plant Physiol 139(3): 1350-1365.
Yalovsky et al., (2008) Regulation of membrane trafficking, cytoskeleton dynamics, and cell polarity by ROP/RAC GTPases. Plant Physiol 147(4): 1527-1543.
Yalovsky et al., (2000) Functional requirement of plant farnesyltransferase during development in *Arabidopsis*. Plant Cell 12(8): 1267-1278.
Zhao et al., (2016) ABA receptor PYL9 promotes drought resistance and leaf senescence. Proc Natl Acad Sci U S A 113(7): 1949-1954.
Zheng et al., (2002) Plasma membrane-associated ROP10 small GTPase is a specific negative regulator of abscisic acid responses in *Arabidopsis*. Plant Cell 14(11): 2787-2797.

\* cited by examiner

FIG. 1

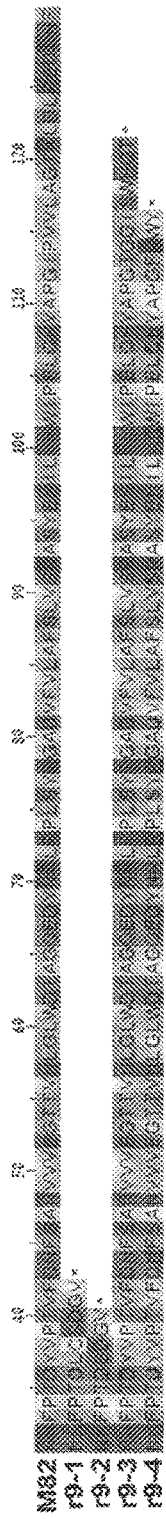

FIG. 4

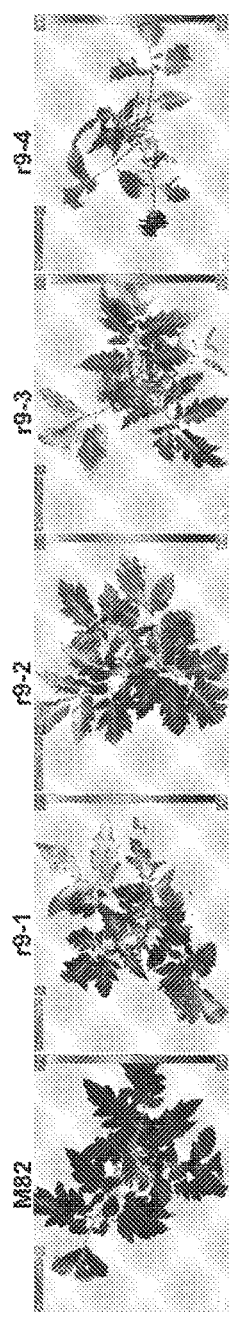
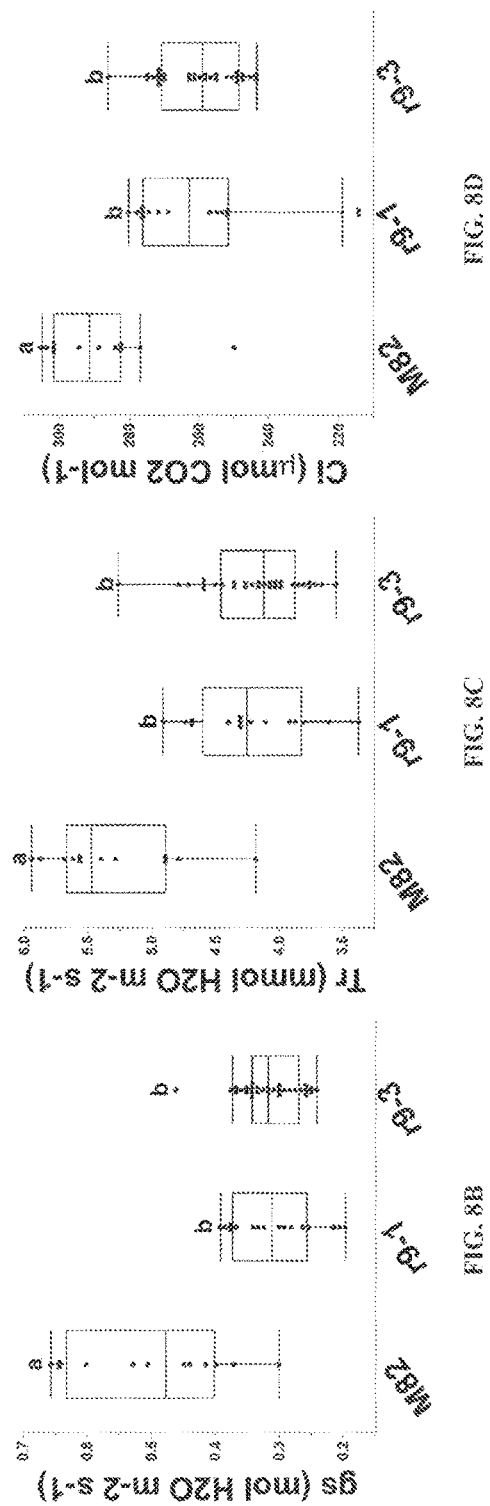
FIG. 8A
FIG. 8B
FIG. 8C
FIG. 8D

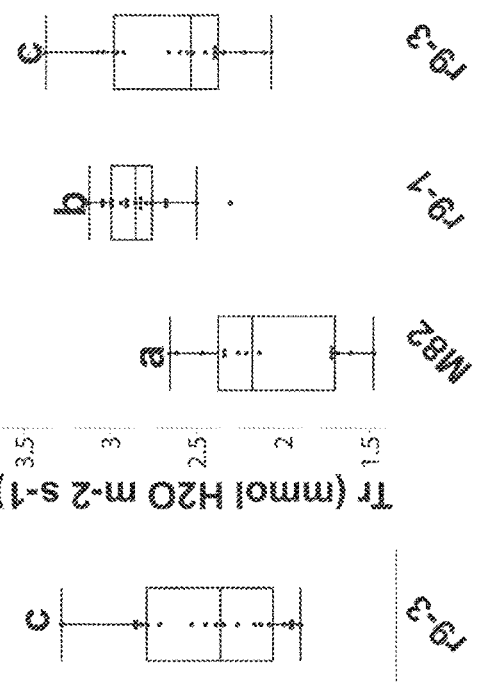
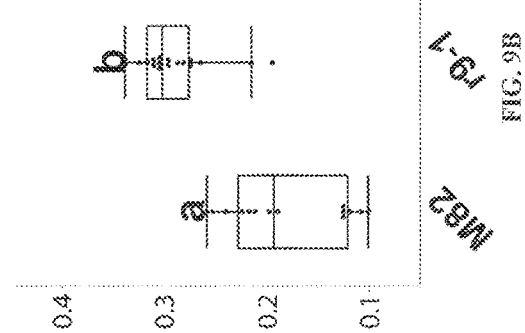
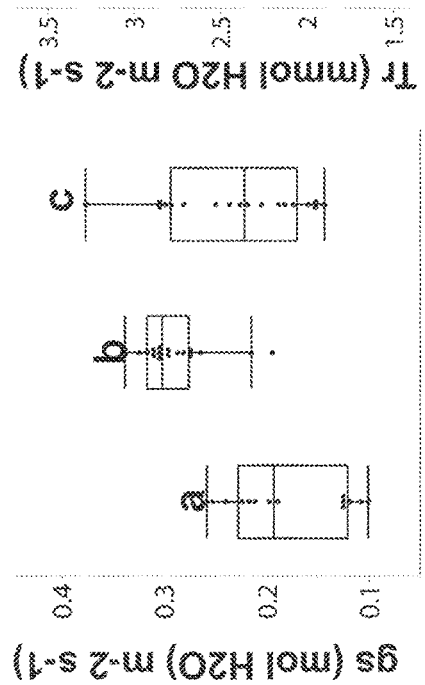
FIG. 9A
FIG. 9B
FIG. 9C

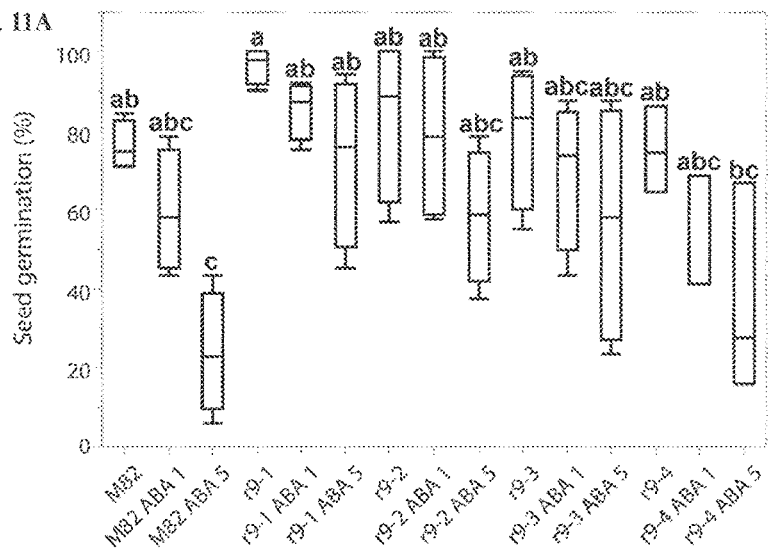
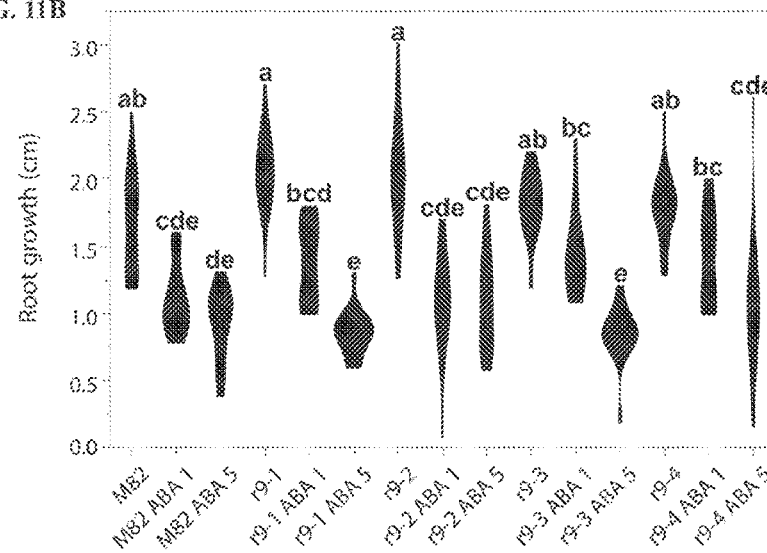
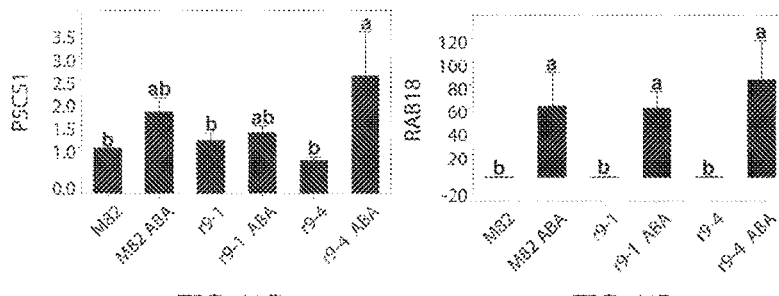
FIG. 11A
FIG. 11B
FIG. 11C
FIG. 11D

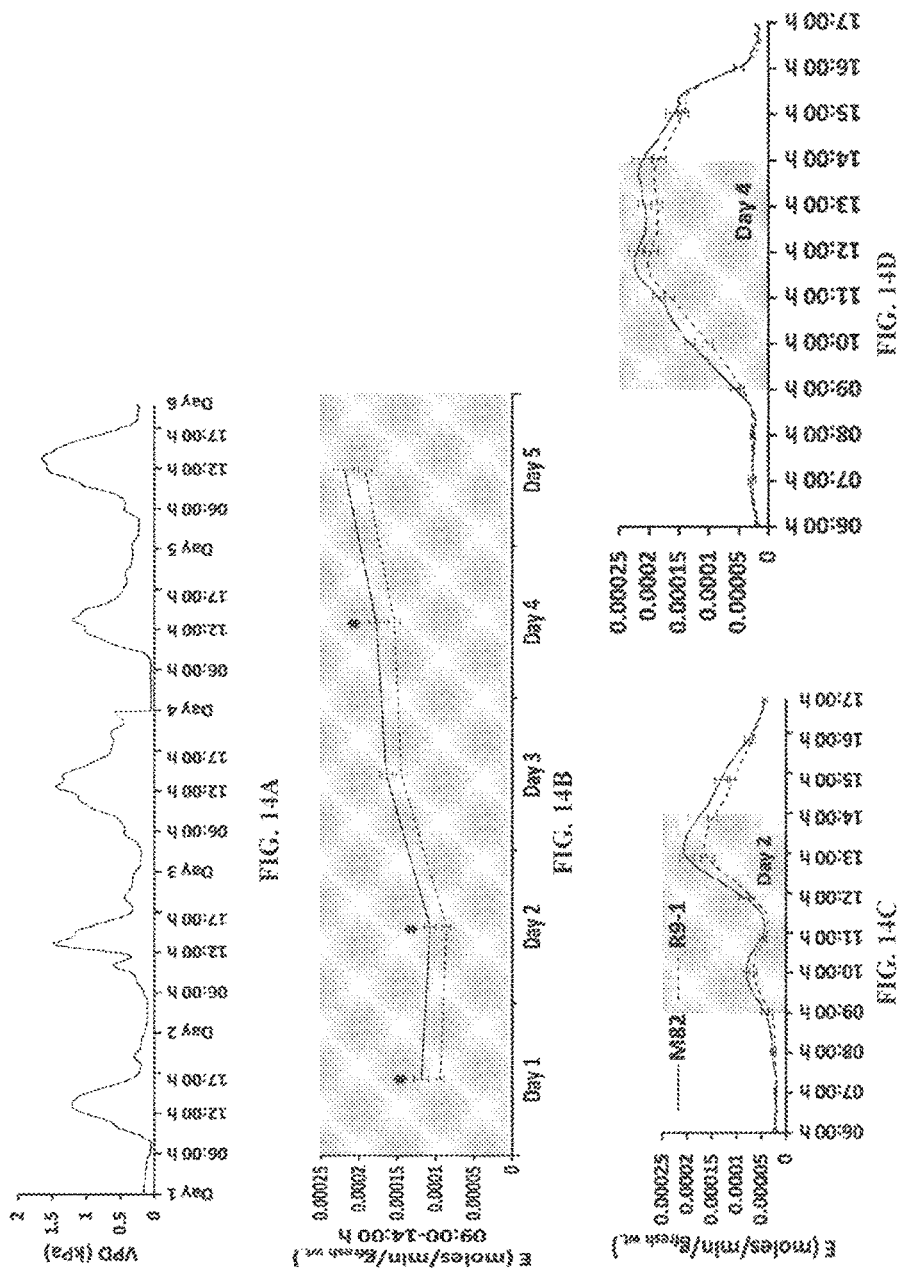

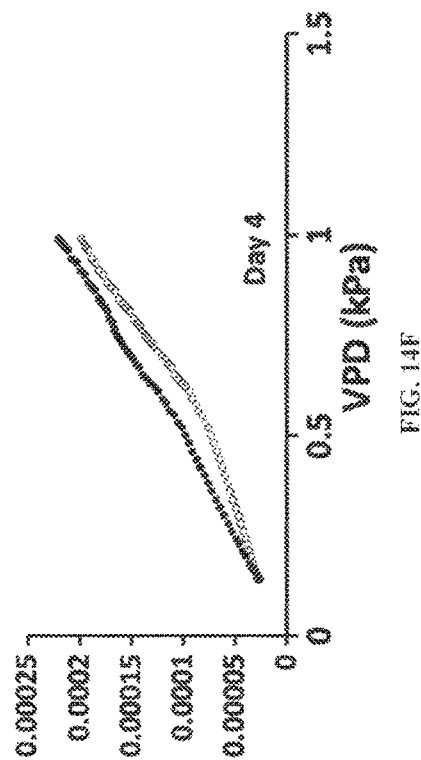
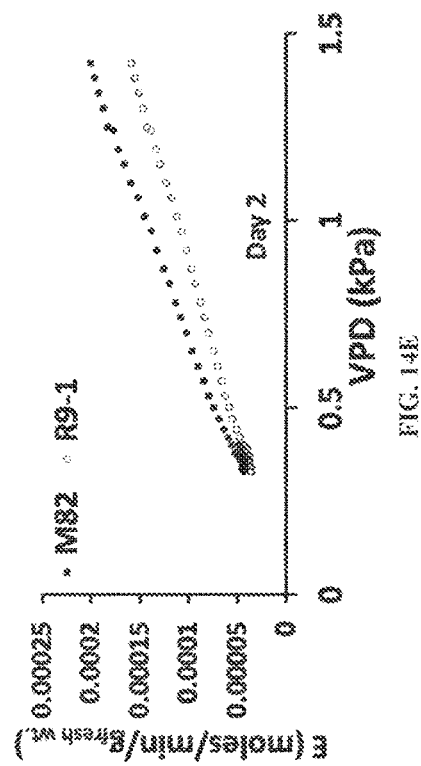
FIG. 14E
FIG. 14F

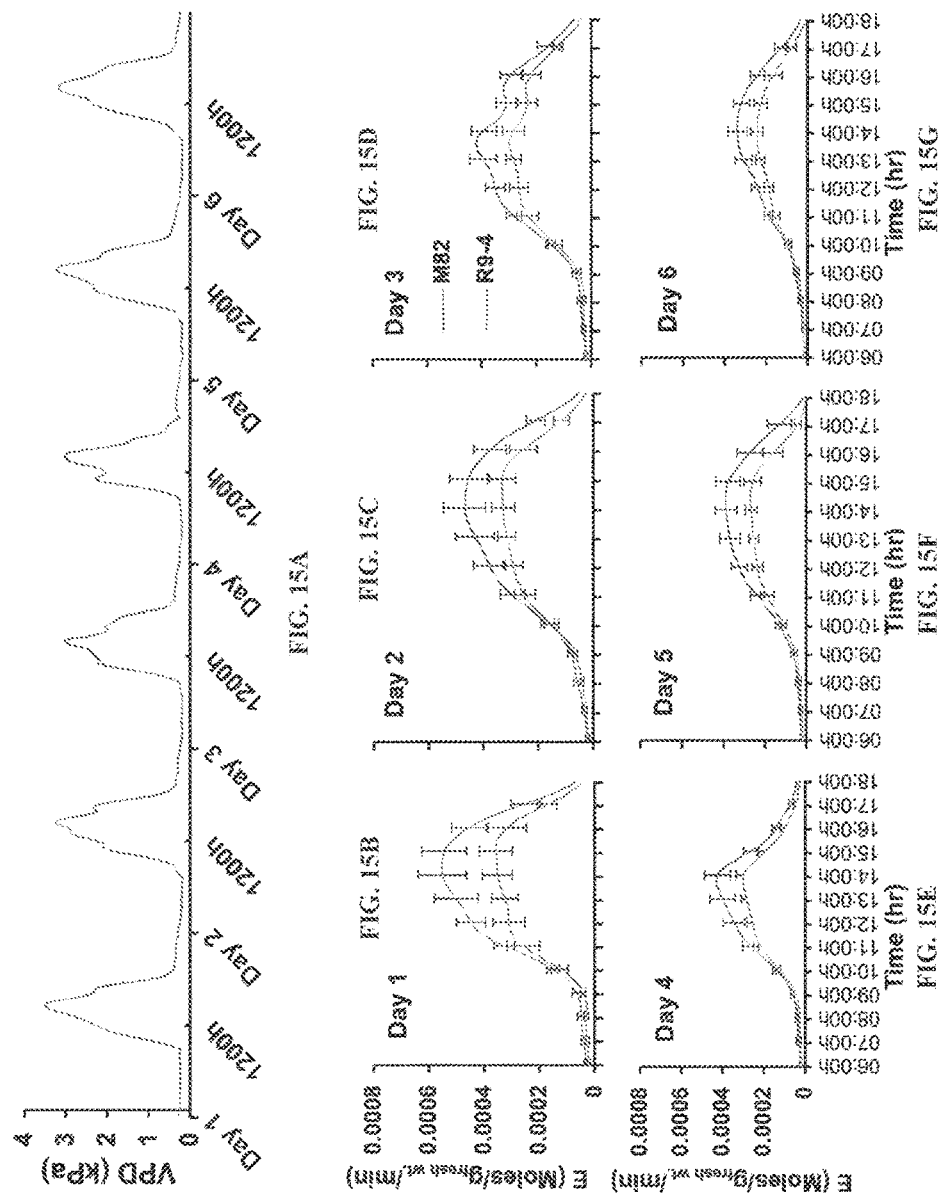

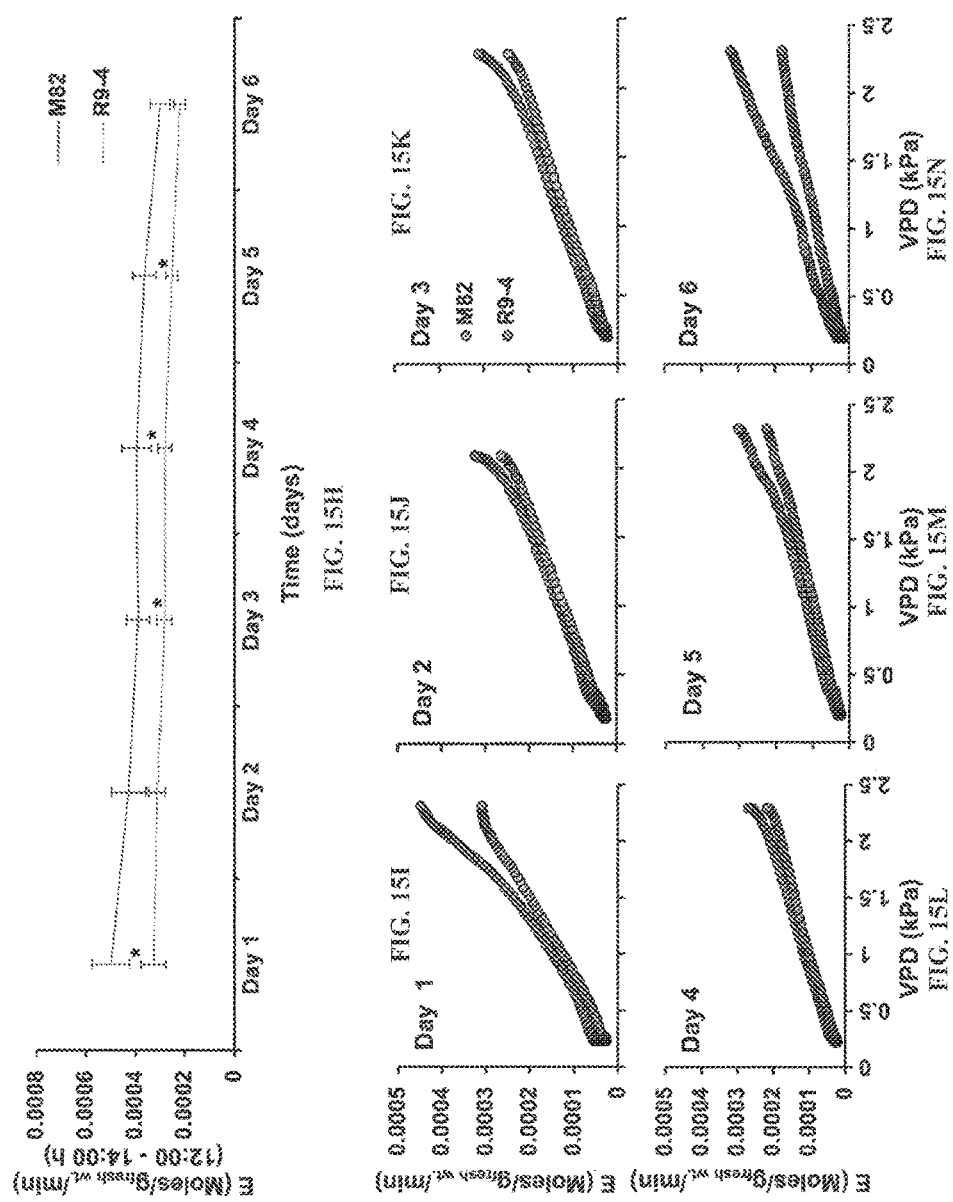

ROP—DEFICIENT PLANTS HAVING HIGH WATER USE EFFICIENCY

The Sequence Listing in ASCII text file format of 30,454 bytes in size, created on Jul. 25, 2024, with the file name "2024-07-31SequenceListing_YALOVSKY1_ST25," filed in the U.S. Patent and Trademark Office on even date herewith, is hereby incorporated herein by reference.

FIELD OF THE INVENTION

The present invention relates to plants, particularly to crop plants including plants of the family Solanaceae having reduced expression and/or activity of SlROP9 protein or homologs thereof, displaying improved water use efficiency and increased tolerance to drought and/or salt stress with minimal effect on the crop yield.

BACKGROUND OF THE INVENTION

Water vapor transpiration from leaves is proportional to the water vapor deficit (VPD). Global warming causes increase in VPD, which in turn results in a higher transpiration rate that negatively affect crop productivity. Transpiration takes place via the stomata pores in the leaf epidermis. The stomata consist of two guard cells that are connected at their edges forming the stomata pore in-between. The stomata pores are also the sites for $CO_2$ uptakes which is assimilated to sugars in photosynthesis. The opening and closing of stomata is a highly regulated process which is sensitive to water stress, $CO_2$ and light. While stomata closure under water-stress conditions reduces water loss via transpiration, it also reduces $CO_2$ uptake and in turn photosynthetic carbon assimilation, which negatively affect the plant growth and yield.

Water-use efficiency (WUE) refers to the ratio between the rate of $CO_2$ assimilation during photosynthesis to the rate of water loss through transpiration in plants. It is typically defined as the number of $CO_2$ molecule assimilated divided by the number of water molecules lost during transpiration at a given unit of time and leaf area, or the amount of carbon assimilated as biomass or yield produced per unit of water used by the plants at a given area. The response of WUE at the leaf level is directly related to the physiological processes controlling the gradients of $CO_2$ and $H_2O$, e.g., leaf to air vapor pressure deficits between the leaf and air surrounding the leaf. On a global scale, about 80% of the fresh water are lost via transpiration by plants. Therefore, and in light of dwindling fresh water resources, WUE in plants is becoming increasingly important, particularly in arid and semiarid regions, for environmentally sustainable food production.

Drought and salt stress are major causes of crop losses and, given projections of global warming, these losses are expected to increase. Plants respond to drought stress by closing of stomata in the leaves, thereby reducing water loss due to transpiration. Under drought, abscisic acid (ABA) levels increase leading to activation of SUCROSE NONFERMENTING RELATED SERINE/THREONINE PROTEIN KINASE (SnRK) family kinases. In guard cells, SnRK2 (also known as OSTI (OPEN STOMATA 1)) phosphorylates SLOW ANION CHANNEL-ASSOCIATED1 (SLAC1), resulting in ion release, turgor loss, and stomata closure. ABA also enhances stomata closure by inducing formation of reactive oxygen species (ROS) by activating the NADPH oxidases (RESPIRATORY BURST OXIDASE HOMOLOGS, RBOH) and by inducing increases in cytoplasmic $Ca^{2+}$ concentrations. In Arabidopsis guard cells, ABA-induced activation of $Ca^{2+}$ channels may require ROS production by RBOHD and RBOHF.

Rho of Plants (ROPs) are the plant-specific family of Rho small GTPases. Arabidopsis encodes 11 ROPs, and tomato encodes nine (Feiguelman, G. et al., Plant Physiol 176, 57-7, 2018). Inactivation of *Arabidopsis* AtROP6 (encoded by At4g35020) by ABA is required for stomata closure (Lemichez E. et al., Genes Dev 15, 1808-1816, 2001). Arabidopsis AtROP10 and AtROP11 mutants are ABA hypersensitive, implicating these ROPs in suppression of ABA responses (Choi, Y. et al., J Plant Biol 57, 245-254, 2014; Xin, Z. et al., Plant Physiol 139, 1350-1365, 2005; Zheng Z. L. et al., Plant Cell 14, 2787-2797, 2002; Li Z et al., J Integr Plant Biol 54, 180-188, 2012; Li, Z. et al., J Integr Plant Biol 54, 169-179, 2012; Li, Z. et al., FEBS letters 586, 1253-1258, 2012). Gain-of-function studies have implicated a rice ROP, OsRAC1, in the activation of OsRBOHB (Wong H. L. et al., Plant Cell 19, 4022-4034, 2007), and ROS formation is correlated with ROP activation (Bloch D., et al., Plant Cell Environ. 34, 76-88, 2011; Duan Q. et al., Nat Commun 5, 3129, 2014; Duan, Q. et al., Proc Natl Acad Sci USA 107, 17821-17826, 2010). Collectively, these studies suggest that ROPs play a central role in stress responses; however, it is unknown why ROP inactivation leads to stomata closure and if and how this is correlated with ROS production in guard cells.

U.S. Application Publication No. 2004/0006783 discloses nucleic acids comprising a heterologous plant promoter operably linked to a polynucleotide encoding a RopGAP polypeptide. The RopGAP polypeptide inactivates Rop GTPase signaling and the heterologous promoter is expressed in a plant tissue other than pollen. In specific embodiments the RopGAP polypeptide comprises a Cdc42/Rac-interactive binding (CRIB) motif and a GAP domain. Plants engineered to express the polypeptide have increased tolerance for low oxygen levels, particularly to flood conditions.

As described hereinabove, there is a great need for crop plants having increased WUE, leading to tolerance of the plants to reduced water availability and even drought and/or salt stress, without significantly compromising the crop plant growth, and more importantly, yield. Furthermore, due to public concern limiting the use of transgenic plants, there is a great and unmet need for drought resistant crop plant that are not classified as transgenic plants.

SUMMARY OF THE INVENTION

The present invention answers the above-described needs, providing plants, particularly crop plants, having increased water use efficiency (WUE) and enhanced drought and/or salt tolerance. The plants of the invention have reduced expression and/or activity of *Solanum lycopersicum* ROP9 (SlROP9) protein or of orthologs thereof, having an increased WUE and drought tolerance compared to plants having active SlROP9 protein or orthologs thereof. Advantageously, the reduced expression and/or activity of SlROP9 or of the orthologs thereof does not negatively affect the crop plant growth and yield.

In particular embodiments, the plants of the present invention comprise inactive mutant of SlROP9 or of orthologs thereof.

The present invention is based, in part, on the unexpected finding that mutations in the SlROP9 gene leading to loss of function of SlROP9 protein increased the WUE of tomato plants bearing the mutations and further the tolerance of the plants to drought, in an abscisic acid (ABA)-independent manner, with negligible effects on photosynthetic $CO_2$ fixation and fruit yield. Without wishing to be bound by any specific theory or mechanism of action, the loss of function of SlROP9 decreased stomata conductance and leaf transpiration, via an increased production of reactive oxygen species in the stomata guard cells. The decreased stomata conductance increases the water use efficiency (WUE) and drought tolerance of the plants.

Due to the lower stomata conductance and lower transpiration observed in plants comprising the Slrop9 mutant, the plants take up less water from the soil. This lower water uptake leads to maintenance of higher water content for longer periods, even under drought conditions, enabling the continuous growth and higher WUE of the plants having reduced expression and/or activity of SlROP9 or its orthologs.

According to a first aspect, the present invention provides a plant or a part thereof comprising at least one cell modified to have reduced expression and/or activity of SlROP9 or an ortholog thereof compared to an unmodified cell, wherein the plant has enhanced water use efficiency compared to a control plant grown under the same conditions.

According to certain embodiments, the plant comprising the at least one modified cell has enhanced tolerance to drought and/or salt stress compared to the control plant.

According to certain embodiments, the control plant does not comprise the at least one modified cell. According to these embodiments, the control plant expresses wild-type SlROP9 or an ortholog thereof. The expression and/or activity level of the SlROP9 or ortholog thereof in the control plant is as typical to the species of said control plant.

According to certain embodiments, the plant is a crop plant.

According to certain embodiments, a wild-type SlROP9 or an ortholog thereof comprises an amino acid sequence at least 80% identical to the amino acid sequence set forth in SEQ ID NO:1. According to certain embodiments, the SlROP9 or the ortholog thereof comprises an amino acid sequence at least 90%, at least 95%, or at least 98% identical to the amino acid sequence set forth in SEQ ID NO:1. According to certain embodiments, the SlROP9 comprises the amino acids sequence set forth in SEQ ID NO:1.

According to some embodiments, the wild type SlROP9 or the ortholog thereof is encoded by SlROP9 gene having a nucleic acid sequence at least 80% identical to the nucleic acid sequence set forth in SEQ ID NO:2. According to some embodiments, the wild type SlROP9 protein is encoded by an SlROP9 gene e having the nucleic acid sequence set forth in SEQ ID NO:2.

Inhibiting the expression of SlROP9 or the gene encoding same may be achieved by various means, all of which are explicitly encompassed within the scope of present invention. According to certain embodiments, inhibiting SlROP9 expression can be affected at the genomic and/or the transcript level using a variety of molecules that interfere with transcription and/or translation including, but not limited to, antisense, dsRNA, miRNA, siRNA, Ribozyme or DNAzyme molecule. According to other embodiments, inhibiting SlROP9 expression is affected by inserting a mutation to the SlROP9 gene, including deletions, insertions, site specific mutations and the like, as long as the mutation results in down-regulation of the gene expression. According to other embodiments, SlROP9 expression is inhibited at the protein level using antagonists, enzymes that cleave the polypeptide and the like.

According to certain exemplary embodiments, the at least one modified cell comprises within its genome at least one mutant allele of SlROP9 or of an ortholog thereof.

The mutant allele of SlROP9 is designated herein Slrop9 allele.

According to certain embodiments, the mutant Slrop9 allele or the mutant ortholog allele confers a loss of function or a reduced function of the encoded SlROP9 protein or encoded ortholog thereof. According to certain embodiments, the encoded SlROP9 protein or ortholog thereof having reduced or null function comprises at least one mutation in at least one domain selected from the group consisting of G-domain, hypervariable domain and a combination thereof.

According to certain exemplary embodiments, the mutant Slrop9 allele comprises a nucleic acid sequence selected from the group consisting of SEQ ID NO:3 (designated rop-9-1), SEQ ID NO:4 (designated rop-9-2), SEQ ID NO:5 (designated rop-9-3), SEQ ID NO: 6 (designated rop-9-4) and homologs thereof. According to some embodiments, the mutant Slrop9 allele encodes non-functional (null) SlROP9 protein having an amino acid sequence selected from the group consisting of SEQ ID NO:7 (ROP-9-1), SEQ ID NO: 8 (ROP-9-2), SEQ ID NO:9 (ROP-9-3), SEQ ID NO:10 (ROP-9-4).

According to certain embodiments, the plant is heterozygous for the mutant Slrop9 allele or the mutant ortholog allele.

According to certain alternative embodiments, the plant is homozygous for the mutant Slrop9 allele or the mutant ortholog allele.

Any method as is known in the art for inserting a mutation into a plant allele, including deletions, insertions, site specific mutations and the like can be used according to the teachings of the present invention, as long as the mutation results in loss of function or reduced function of the encoded protein.

According to certain embodiments, the mutation is a site-specific mutation inserted by a gene-editing method using artificially engineered nucleases.

According to certain embodiments, the artificially engineered nucleases are selected from the group consisting of meganucleases, Zinc finger nucleases (ZFNs), transcription-activator like effector nucleases (TALENs), and CRISPR/Cas, CRISPR/Cas homologous and CRISPR/Cas modified systems.

Insertion of site-specific mutations, particularly using gene-editing system, has the advantage of designing mutagenesis tools that do not have off-target effects.

Thus, according to certain exemplary embodiments, the plants of the invention having enhanced water use efficiency are obtained by inserting a mutation within at least one allele of SlRO9 or an ortholog thereof using CRISPR/Cas system.

Since most genome-editing techniques can leave behind minimal traces of DNA alterations evident in a small number of nucleotides as compared to transgenic plants, crop plants created through gene editing could avoid the stringent regulation procedures commonly associated with genetically modified (GM) crop development, and are typically defined as non-transgenic crop plants.

According to certain exemplary embodiments, the plants of the present invention having enhanced water use efficiency are non-transgenic plants.

According to certain alternative embodiments, the plants of the present invention are transgenic plants. According to these embodiments, the at least one modified cell comprises silencing molecule targeted to SlROP9 or to an ortholog thereof is selected from the group consisting of RNA interference (RNAi) molecule and antisense molecule.

According to certain embodiments, the RNAi molecule is selected from the group consisting of microRNA (miRNA), small interfering RNA (siRNA), short-temporal RNA (stRNA), double-stranded RNA (dsRNA), and short-hairpin RNA (shRNA).

According to certain embodiments, the silencing molecule is targeted to SlROP9 encoding gene or an ortholog thereof comprising a nucleic acid sequence at least 80% identical to SEQ ID NO:2.

According to certain embodiments, the expression and/or activity of the SlROP9 protein or the ortholog thereof is reduced by at least 60%, at least 70%, at least 80%, or at least 90%. According to some embodiments, the expression and/or activity is reduced by 100%.

According to certain embodiments, the WUE of a plant of the invention comprising at least one cell with reduced expression and/or activity of SlROP9 or ortholog thereof is at least 10%-20% higher compared to the WUE of the control plant under irrigation conditions. Due to their increase WUE, the Slrop9 mutant plants require less irrigation.

According to certain embodiments, symptoms of leaf wilting of the plants of the invention comprising at least one cell with reduced expression and/or activity of SlROP9 or ortholog thereof, when exposed to drought or salt stress conditions, are reduced by at least 10%-50% compared to leaf wilting symptoms of a plant comprising wild-type SlROP9 allele grown under the same stress conditions.

According to certain embodiments, the crop plant is selected from a plant producing fruit; flower and ornamental plant; grain producing plant, including, but not limited to wheat, oats, barely, rye, rice, and maize; legumes, including, but not limited to peanuts, peas, soybean, and lentil; plant producing forage; plant producing fiber, including, but not limited to cotton and flax; a tree for wood industry; plant producing tuber or root crop; sugar beet; sugar came; plant producing oil, including, but not limited to canola, sunflower, and sesame; plants used for their leaves including but not limited to parsley, lettuce, kale, spinach, and tobacco. Each possibility represents a separate embodiment of the present invention.

According to certain embodiments, the crop plant is of the family Solanaceae.

According to certain exemplary embodiments, the Solanaceae crop plant is selected from the group consisting of tomato (*Solanum lycopersicum*), eggplant (*Solanum melongena*) potato (*Solanum tuberosum*) and tobacco (*Nicotiana tabacum*). According to certain currently preferred embodiments, the crop plant is tomato plant.

The present invention further provides seeds, fruit, or any other part of the plants of the invention having enhances WUE, as well as cells and tissue cultures derived thereof and plants regenerated therefrom.

According to certain embodiments, the present invention provides a seed of the plant of the invention having enhances WUE, wherein a plant grown from the seed comprises at least one modified cell with reduced expression and or activity of SlROP9 protein or of an ortholog thereof compared to an unmodified cell, wherein the SlROP9 protein comprises an amino acid sequence at least 80% identical to the amino acid sequence set forth in SEQ ID NO:1.

According to another aspect, the present invention provides a method for producing a plant with enhanced water use efficiency, the method comprising reducing the expression and/or activity of SlROP9 or an ortholog thereof within at least one cell of the plant. According to certain embodiments, the method results in a plant having enhanced tolerance to drought or salt stress compared to a corresponding wild type plant having unmodified expression of SlROP9.

According to certain embodiments, the method comprises introducing at least one mutation in at least one wild-type allele of SlROP9 or an ortholog thereof to form Slrop9 mutant allele, wherein the at least one mutation confers a loss of function or reduced function of the encoded protein.

According to certain embodiments, the wild-type SlROP9 allele encodes an SlROP9 protein having the amino acid sequence set forth in SEQ ID NO:1, or a homolog of SlROP9 protein having an amino acid sequence at least 80% identical to SEQ ID NO:1.

According to certain exemplary embodiments, the wild-type SlROP9 allele comprises a nucleic acid sequence at least 80% identical to SEQ ID NO:2.

According to certain embodiments, the at least one mutation is selected from the group consisting of an insertion, a deletion and a combination thereof.

According to certain exemplary embodiments, the at least one mutation results in a truncated protein. According to certain exemplary embodiments, the truncated protein lacks the SlROP9 wild-type G-domain or a part thereof. According to these embodiments, the mutation confers loss of function of the encoded protein.

According to certain embodiment, the at least one mutation is induced by genome editing using at least one artificially engineered nuclease. According to certain embodiments, the artificially engineered nuclease is selected from the group consisting of meganucleases, Zinc finger nucleases (ZFNs), transcription-activator like effector nucleases (TALENs) and CRISPR/Cas systems, including CRISPR/Cas homologous and CRISPR/Cas modified systems.

According to certain currently exemplary embodiments, the present invention provides a method for producing a plant with enhanced water use efficiency, the method comprising inducing at least one mutation in a wild-type allele of SlROP9 or an ortholog thereof to form Slrop9 mutant allele, wherein the at least one mutation confers a loss of function or reduced function of the encoded protein, and wherein the at least one mutation is induced by CRISPR/Cas system.

According to yet alternative embodiments, reducing the expression of SlROP9 or the ortholog thereof is obtained by transforming at least one cell of the plant with at least one silencing molecule targeted to said SlROP9 or ortholog thereof having a nucleic acid sequence at least 80% identical to the nucleic acid sequence set forth in SEQ ID NO:2.

Also encompassed herein are plants produced by the methods of the invention, parts thereof and plants regenerated from same.

It is to be understood that any combination of each of the aspects and the embodiments disclosed herein is explicitly encompassed within the disclosure of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 shows sequence alignment of SlROP9 (SEQ ID NO:1) and wild tomato (Sopen (*Solanum pennellii*), SEQ ID NO:31) with eggplant (Sme (*Solanum melongena*), SEQ ID NO: 32) and two *Arabidopsis* homologues AtROP10 (SEQ ID NO:33) and AtROP11 (SEQ ID NO:34).

FIG. 2 shows subcellular localization of GFP-SlROP9 and SlROP9 interaction with *Arabidopsis* and tomato ICR (Interactor of Constitutively active ROP) homologs.

Figure 4:
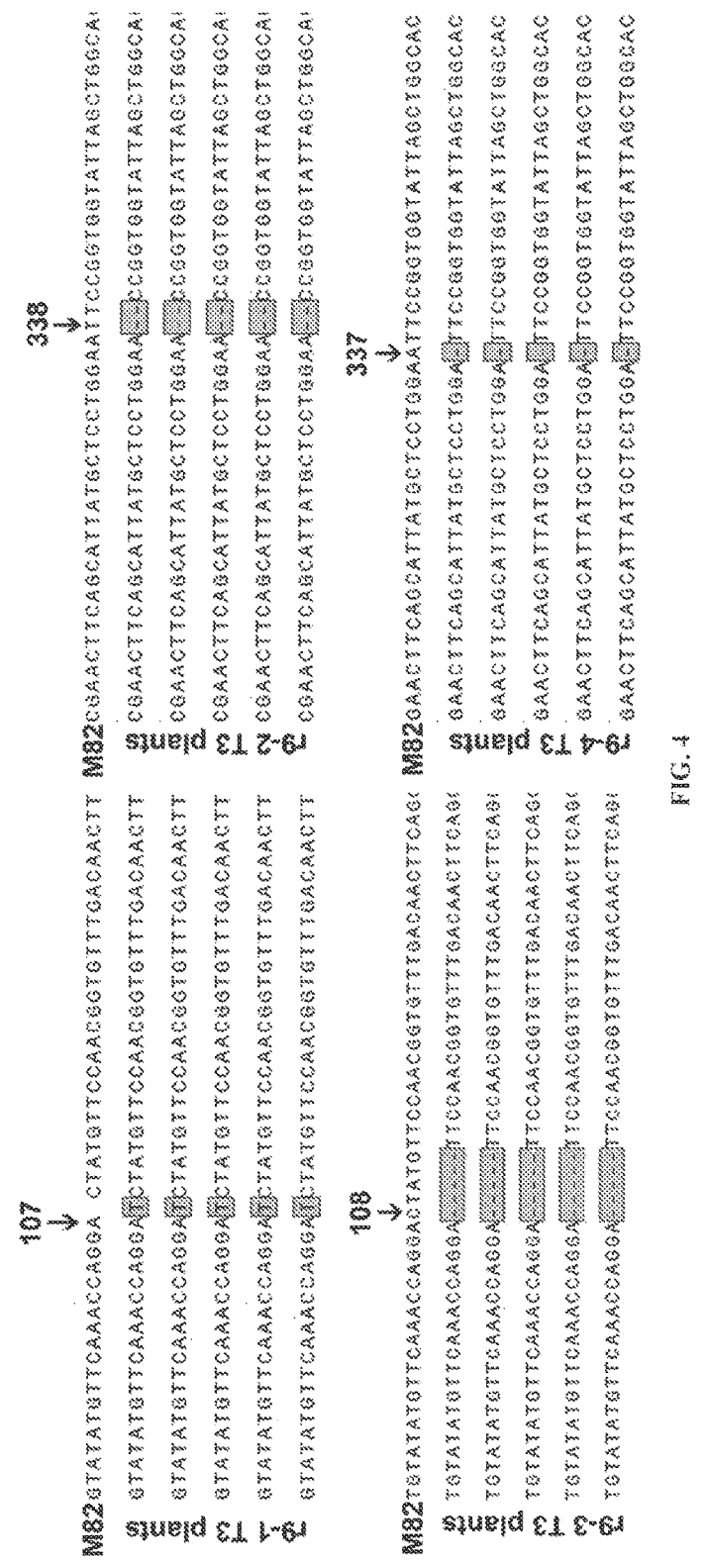

FIG. 4 is a schematic presentation of segregation of the mutations induced by CRISPR/Cas9 and sgRNAs complementary to Slrop9. Nucleotide sequences around the PAM sites of rop9-1 (SEQ ID NO:47) and corresponding M82 wild type (SEQ ID NO: 46), rop9-2 (SEQ ID NO:51) and corresponding M82 wild type (SEQ ID NO:50), rop9-3 (SEQ ID NO:49) and corresponding M82 wild type (SEQ ID NO:48), and rop9-4 (SEQ ID NO:53) and corresponding M82 wild type (SEQ ID NO:52) from five individual T3 plants from each allele, confirming homozygosity for the mutations. The sites of insertions or deletions are indicated by arrows. The numbers denote nucleotide number where the InDel occurred. The mutated regions deleted are highlighted by gray boxes.

FIG. 5 demonstrates that fruit number, size and BRIX of field grown plants are not reduced in rop9 mutants. Analysis was carried out on M82, rop9-3 (19-3) and rop9-4 (19-4) plants gown in an experimental field plot during March-June 2020. FIGS. 5A, B, C and F: Letters above bars note variance groups calculated in all assays with one-way ANOVA and Tukey-Kramer HSD, $p \leq 0.05$; FIGS. 5D and F, Student's t-test, * notes $p \leq 0.05$ between r9-4 and M82.

FIG. 8 shows that the rop9 mutants have reduced transpiration, stomata conductance with negligible effects on photosynthesis. FIG. 8A: Infrared thermal images of 4-week-old M82 and rop9 mutants irrigated 12 h prior to imaging. Temperature ranges were set between 17-21° C. FIG. 8B-E: stomata conductance, leaf transpiration rate, internal leaf $CO_2$ levels, and the rates of photosynthetic $CO_2$ assimilation measured with a LI-6400XT portable gas-exchange device. FIG. 8B: stomata conductance (gs), FIG. 8C: transpiration rate (Tr), and FIG. 8C: intercellular $CO_2$ concentration (Ci) was measure in 4-week-old plants ($p \leq 0.0001$ (FIG. 8B-D). FIG. 8E: Photosynthetic $CO_2$ assimilation rate ($A_N$) in M82, rop9-1 (19-1), and rop9-3 (r9-3) plants. The differences were not significant. FIG. 8F: Intrinsic water use efficiency (iWUE) ($p \leq 0.05$). Data in B, C and E are normalized to leaf area ($m^{-2}$) and time ($s^{-1}$). In B-F, the boxes are interquartile range, the whiskers are the $1^{st}$ and $4^{th}$ quartiles, the line median and the black dots are all the measurements taken. Letters above bars note variance groups calculated in all assays with one-way ANOVA and Tukey-Kramer HSD.

FIG. 9 shows transpiration and stomata conductance of rop9 and M82 WT under drought. FIG. 9A: IR images of M82 WT the four rop9 mutant alleles (rop9-1 (19-1), rop9-2 (r9-2), rop9-3 (19-3) and rop9-4 (r9-4)) following three days without watering (drought, 3d). Stomata conductance and transpiration of rop9 mutants was higher following 3 days of drought. Stomata conductance (gs) (FIG. 9B) and transpiration rate (Tr) (FIG. 9C) of mutants and M82 plants. Box plots are upper and lower quartiles, whiskers upper and lower extreme. Letters above plots note variance groups ($p < 0.05$) calculated for all assays with, ANOVA and Tukey Kramer HSD.

FIG. 11 demonstrates that the rop9 mutants are not ABA hypersensitive. FIG. 11A: Percent of seeds that germinated on mock-treated (0.1% ethanol) medium or on media supplemented with 1 μM ABA (ABA 1) or 5 μM ABA (ABA 5). Data are from four biological replicates (n=51 for three replicates or n=40 for one replicate) (p≤0.05). FIG. 11B: Primary root elongation in mock-treated (0.1% ethanol), 1 μM ABA-treated (ABA 1), and 5 μM ABA-treated (ABA 5) seedlings. Data are from three biological replicates (n=14 to 16) (p≤0.05). FIG. 11C-D: QPCR of ABA-responsive genes P5CS1 (Solyc06g019170) (FIG. 11C) and SlRAB18 (Solyc02g084850) (FIG. 11D) in mock (0.1% ethanol) or 50 μM ABA-treated M82, rop9-1 (r9-1), and rop9-4 (r9-4) cotyledons (p≤0.05). Letters above bars and plots are variance groups calculated in all assays with one-way ANOVA and Tukey-Kramer HSD (p≤0.05).

FIG. 12 shows that activation of NADPH oxidase in the rop9 mutants results in elevated ROS levels in guard cells and reduced stomata aperture.

FIG. 14 shows the effect of ROP9 knocked-out on continuous whole plant transpiration (E) in a greenhouse experiment. FIG. 14A: Daily vapor pressure deficit (VPD) during the 5 days of experiment. FIG. 14B: Midday mean±SE E (normalized transpiration rate) during 5 days from 0900 to 1400 h. FIG. 14C and FIG. 14D: Mean±SE diurnal E (normalized transpiration rate) from 0600 to 1700 h during day 2 and day 4 respectively. FIG. 14E and FIG. 14F: Correlation between E and VPD at time of VPD increase (from low till the time of highest reached peak of E during the midday in FIGS. 14C and D respectively) during day 2 (from 1130 to 1330) and day 4 (from 0830 to 1130) respectively. R9-1: rop9-1. Asterisk represent significant differences using student t-test (p≤0.05, n=6).

FIG. 15 shows the effect of ROP9 knocked-out (R9-4) on continuous whole plant transpiration (E) in a greenhouse experiment. FIG. 15A: Daily vapor pressure deficit (VPD) during the 6 days of experiment. FIG. 15B-G: Mean±SE diurnal E (normalized transpiration rate) from 0600 to 1800 h during days 1 to 6, respectively. FIG. 15H: Midday mean±SE E (normalized transpiration rate) during 6 days from 1200 to 1400 h. FIG. 15 I-N: Correlation between E and VPD at time of VPD increase (from 08:30 to 13:30, from low till the time of high peak of E during the midday in FIG. 15B-G, respectively). Asterisk represent significant differences using Student's t test (p≤0.05, M82 n=4 and rop9-4 (19-4) n=5).

FIG. 16 demonstrates the effect of ROP9 knock-out on continuous whole plant transpiration (E) in greenhouse experiment.

DETAILED DESCRIPTION OF THE INVENTION

Figures 2A, 2B:
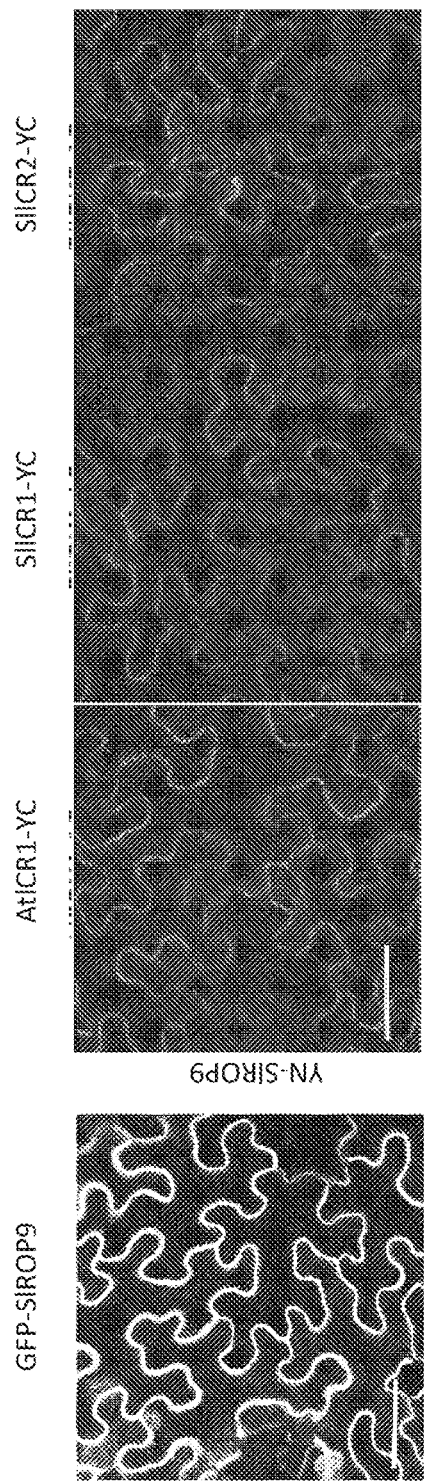
FIG. 2A: A maximum intensity Z-stack image showing that GFP-SlROP9 was localized in the plasma membrane following ectopic expression in *N. benthamiana* leaf epidermal cells.
FIG. 2B: BiFC (Bimolecular Fluorescence Complementation) assays showing interaction between YN-SlROP9 and *Arabidopsis* and tomato ICRs AtICR1, SlICR1 (Solyc12g011360.1.1), and SlICR2 (Solyc07g056650.2) fused to YC. Scale bars: 50 μm. YN and YC refer to the N and C-terminal halves of YFP, respectively.

The present invention provides plants, particularly crop plants, which show reduced transpiration upon increased vapor pressure deficit at mid-day, with negligible effects on photosynthesis, growth and fruit production. Thus, the plants of the invention display high water use efficiency (WUE) leading to tolerance to sub-optimal soil water content (drought or water stress) and/or to sub-optimal soil salinity (salt stress). The enhanced WUE is attributed to a reduced function or loss of function of Rho of Plant (ROP) protein in the plant of the invention. Exemplified in tomato plants (*Solanum lycopersicum*), guard cells comprising null ROP (SlROP9) activity constitutively produce reactive oxygen species (ROS) in an NADPH oxidase-dependent manner, leading to stomata closure at high water vapor deficiency (VPD) without increasing general ABA responses. Since SlROP9 homologs in a variety of plant species (SlROP9 orthologs) are highly conserved, reducing the expression and/or activity of SlROP9 or orthologs thereof according to the teachings of the present invention leads to improved crop water use efficiency and drought and/or salt tolerance.

Definitions

The term "plant" is used herein in its broadest sense. It includes, but is not limited to, any species of woody, herbaceous, perennial or annual plant. It also refers to a plurality of plant cells that are largely differentiated into a structure that is present at a stage of the plant development capable of producing crop.

As used herein, the term "crop plant" refers to a plant with at least one part having commercial value. The term encompasses plants producing edible fruit (including vegetables), plants producing grains (as a food, feed and for oil production), plant producing flowers and ornamental plants, legumes, root crops, tuber crops, leafy crops and the like.

As used herein, the terms "control plant" refers to a plant comprising within its genome a gene encoding SlROP9 or an ortholog thereof, wherein the expression of the SlROP9 or its ortholog has not been artificially modified. The control plant is also termed "a plant expressing wild type SlROP9 or an ortholog thereof". It is to be explicitly understood that the control plant can comprise other modifications, for example modified expression and/or activity of proteins other that SlROP9 or its orthologs. According to certain embodiments, the control plant is of the same species. As exemplified hereinbelow, four independent mutant alleles of SlROP9 were generated and analyzed, and all displayed the same increased WUE phenotype. These mutants thus demonstrate that the increased WUE is associated with the loss of function of SlROP9 alone.

The terms "drought" and "drought stress" are used herein interchangeably and refer to sub-optimal soil hydration conditions for the growth of a particular plant species. Soil hydration can be measured by various methods as is known to a person skilled in the art, depending on the soil type. According to certain embodiments, the soil water content is measured relative to the maximum amount of water that a given soil can retain ("field capacity") as weight/weight percentage. According to these embodiments, drought conditions refer to soil water content of less than 70% of field capacity.

The term "water use efficiency" as used herein refers to the ratio of photosynthetic $CO_2$ assimilation rate (which may be measured by aerial biomass yield) to water use or stomata conductance (which may be measured by gas exchange from leaf).

According to certain embodiments, "enhanced WUE" as used herein refers to at least about 10%, at least about 15%, at least about 20%, at least about 25%, at least about 30%, at least about 35%, at least about 40%, at least about 45%, at least about 50% or more of the WUE of the plant of the present invention compared to a control plant grown under the same growth conditions. According to certain exemplary embodiments, the WUE of the plants of the present invention is at least about 10%-20% higher compared to the WUE of the control plant under irrigation conditions.

As used herein, the term "salt stress" refers to soil salinity conditions leading to sub-optimal growth of a particular plant species. The term "soil salinity" refers to the salt concentration of the soil solution in terms of g/l or electric conductivity (EC) in dS/m. EC of 5 is about 60 mM NaCl; EC of 10 is about 120 mM NaCl and of EC 12.5 is about 250 mM NaCl. Sea water may have a salt concentration of 30 g/l (3%) and an EC of 50 dS/m. Soils are considered saline when the EC>4. When 4<EC<8, the soil is called moderately saline and when 8<EC the soil is called highly saline.

It is to be understood that different plant species show different response to a certain abiotic stress, particularly to soil salinity and soil water content. Accordingly, as used herein the terms "a plant having an enhanced tolerance" or "a plant having an enhanced resistance" refer to at least about 1%, at least about 2%, at least about 3%, at least about 4%, at least about 5%, at least about 10%, at least about 15%, at least about 20%, at least about 30%, at least about 40%, at least about 50%, at least about 60%, at least about 70%, or at least about 80% and more increase in the plant abiotic stress tolerance as measured by at least one of growth, biomass, yield, fertilizer use efficiency and water use efficiency of the plant of the invention (i.e. a plant having a reduced expression and/or activity of SlROP9 or of an ortholog thereof) compared to a corresponding wild type plant of the same species having normal expression of ROP9, wherein both plants are grown under the same normal or stress conditions. According to certain embodiments, an enhanced tolerance to salt or drought stress refers to at least from about 5% to about 100%, or from about 10% to about 100%, or from about 20% to about 100% enhancement in at least one parameter selected from the group consisting of growth, biomass, yield, fertilizer use efficiency, water use efficiency and any combination thereof.

As used herein, the term "ortholog" refers to homologous genes in different species that evolved from a common ancestral gene. Accordingly, orthologs typically retain the same function during the course of evolution. In the context of the present invention, SlROP9 ortholog is a protein of a plant species other than *Solanum lycopersicum* having the function of SlROP9. According to certain embodiments, the SlROP9 ortholog comprises an amino acid sequence at least 90% identical to SEQ ID NO:1. It is to be explicitly understood that a reference throughout the instant specification to a plant comprising SlROP9 or mutants thereof encompasses SLROP9 orthologs or mutants thereof.

Homology (e.g., percent homology, sequence identity+sequence similarity) can be determined using any homology comparison software computing a pairwise sequence alignment.

As used herein, "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff JG. (Amino acid substitution matrices from protein blocks. Proc. Natl. Acad. Sci. U.S.A. 89 (22), 10915-9, 1992).

Identity (e.g., percent homology) can be determined using any homology comparison software, including for example, the BlastN, BlastX or Blastp software of the National Center of Biotechnology Information (NCBI) such as by using default parameters.

According to some embodiments of the invention, the identity is a global identity, i.e., an identity over the entire amino acid or nucleic acid sequences of the invention and not over portions thereof.

According to some embodiments of the invention, the term "homology" or "homologous" refers to identity of two or more nucleic acid sequences; or identity of two or more amino acid sequences; or the identity of an amino acid sequence to one or more nucleic acid sequence.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The terms "polynucleotide", "polynucleotide sequence", "nucleic acid sequence" and "isolated polynucleotide" are used interchangeably herein. These terms encompass isolated nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

The system used in the present invention, enabling continuous as well as momentary measurements of plant transpiration (E), allows analysis of E throughout the day from sunrise (06:00 hours) to sunset (17:00 hours). The plant response to increase in VPD that takes place from early morning and peaks at midday can thus be followed (FIG. 14A). In accordance with the results obtained at the cell and tissue and organ levels the whole plant transpiration of r9-1 plants was significantly lower than M82 during the midday hours (FIG. 14B). Remarkably, the difference in E between the lines were most visible during midday hours (FIGS. 14B, C and D; gray background and 16A and 16B) while no differences in transpiration rate were seen at early morning or evening hours (FIGS. 14C, and D). Moreover, the analysis revealed differences in the response of the whole plant E to daily rise in VPD as represented by E to VPD plots (FIGS. 14E and F). Similar results were obtained with rop9-4 in an independent experiment. Namely, the transpiration of rop9-4 mutants was lower compared to control plants especially during mid-day hours with the surge in VPD (FIG. 15). Thus, it seems that rop9-1 and rop9-4 plants are able to normally allow $H_2O$ and $CO_2$ diffusion at early morning hours before the large surge in VPD (i.e., increase in water loss), while maintaining relative lower E, at conditions of increased water loss. Without wishing to be bound by any specific theory or mechanism of action, this behavior can explain the higher WUE of the rop9 mutants as compared to wild-type M82 tomato plants and the ability of rop9 mutants to maintain similar shoot weight and yield component as M82 under well irrigation conditions (FIGS. 5 and 16).

The combination of drought and high temperature is deleterious to yield because under drought, plants close their stomata and as a result the leaf temperatures increases (FIG. 8A). At high ambient temperatures, increased leaf temperature often results in leaf death which reduces the yields. Because the Slrop9 mutant plants can transpire also under drought conditions, they maintain their leaf temperatures lower compared to wild type under these stress conditions and therefore survive better. As is shown in FIG. 3, after 7 days of drought the Slrop9 mutant plants recovered within an hour while the wild type M82 plants did not.

In summary, plants comprising the Slrop9 mutants have at least two advantages related to water management: 1) due to their higher WUE they require less irrigation and 2) due to the lower transpiration and stomata conductance they take up less water from the soil on which they are grown and this help to keep the deeper soil layer(s) with higher humidity, allowing the roots of the plant to take up water from the soil for longer period of the drought conditions. For this reason, under drought the transpiration and stomata conductance of the Slrop9 mutants was maintained higher compared to wild type plant, as the deeper soil layer kept moist and the plants did not experience the same stress that the wild type (M82) plants sensed (FIG. 8).

According to an aspect of the present invention, there is provided a plant or a part thereof comprising at least one cell modified to have reduced expression and/or activity of SlROP9 or of an ortholog thereof compared to an unmodified cell, wherein the plant has enhanced water use efficiency compared to a control plant grown under the same conditions.

According to certain embodiments, the plant comprising the at least one modified cell has enhanced tolerant to drought and/or salt stress. According to certain embodiments, the increased drought and/or salt tolerance is in comparison with a control plant, not comprising a modification in the SlROP9 expression or activity. The rate of the expression or activity of SlROP9 or of an SlROP9 ortholog in the control plant is a rate typical to the plant species comprising the wild type SlROP9 or ortholog thereof.

As used herein, the expression and/or activity of SlROP9 or of the ortholog thereof is "reduced", "inhibited", "down regulated" or "knocked out" or "knocked down" if the level of the protein or its measured activity is reduced by at least 60%, at least 65%, at least 70%, at least 75%, at least 80%, at least 85%, at least 90%, at least 91%, at least 92%, at least 93%, at least 94%, %, at least 95%, at least 96% at least 97%, at least 98%, at least 99%, or more compared to its level in a control plant or compared to a predetermined threshold level. According to some embodiments, the term "reduced expression and/or activity" refers to 100% inhibition or "loss of function" or "null function" protein.

According to certain exemplary embodiments, the WUE of a plant of the invention or its tolerance to draught and/or salt stress in "increased" or "enhanced" wherein the WUE or tolerance to drought or slat stress in enhanced by at least about 10%, at least about 11%, at least about 12%, at least about 13%, at least about 14, at least about 15%, at least about 16%, at least about 17%, at least about 18%, at least about 19%, or by at least about 20% compared to the WUE or tolerance of a control plant or a predetermined level.

The control plant is as defined herein.

According to certain currently exemplary embodiments, the at least one modified cell comprises within its genome a mutant of at least one SlROP9 allele or a mutant of at least one SlROP9 ortholog allele. The mutant allele is designated herein interchangeably as "Slrop9", "Slrop9 allele" and "Slrop9 mutant allele". Same designation is used for the mutant ortholog allele ("Slrop9 ortholog", "Slrop9 ortholog allele" and "Slrop9 ortholog mutant allele"). The mutation can be a nucleotide(s) insertion, deletion, or substitution as is known in the art.

According to certain embodiments, the mutant allele comprises at least one mutation. According to certain embodiments, the at least one mutant allele encodes a mutant SlROP9 protein or an ortholog thereof, wherein the mutation disrupts at least one of the protein G-domain, the protein hypervariable domain or a combination thereof.

The Ras superfamily small G proteins of which SlROP9 is a member, are composed of two major domains: the conserved G-domain which is responsible for nucleotide (GDP/GTP) binding and hydrolysis and effector (protein targets) binding, and a less conserved C-terminal hypervariable domain which is responsible for membrane anchoring (e.g. Yalovsky et al., Plant Physiology, 147, 1527-1543, 2008). The G-domain of ROPs is typically of about 15-20 kDa. Mutation(s) within the G-domain which interrupt the protein core mechanism of the GDP/GTP binding and hydrolysis, effector binding and activation-dependent S-acylation (of conserved G-domain cysteine residues) will result in a loss of function of the protein. In addition, proper activity of ROPs depends on intact hypervariable domain, since attachment to the membrane is necessary for the activity. In particular, mutations within the Carboxy-terminal end of the hypervariable domain, which eliminate the Carboxy-terminal lipid modified cysteine residues or reduce the number of positive-charged amino acids such as lysine and arginine, would compromise the interaction of ROPs with the membrane and reduce or eliminate the protein activity. The mutated SlROP9 proteins exemplified herein are all truncation mutants in the G-domain and are inactive and considered as null mutants.

According to certain embodiments, the mutant Slrop9 allele encodes a non-functional SLROP9 or its ortholog protein, also referred to herein as null SlROP9 or null ortholog thereof.

According to certain alternative embodiments, the at least one cell is a transgenic cell comprising at least SlROP9-silencing molecule, including antisense and RNAi molecule(s).

According to additional alternative embodiments the SlROP9 expression and/or activity is inhibited at the protein level using antagonists, enzymes that cleave the polypeptide and the like.

According to certain embodiments, the wild-type SlROP9 or the ortholog thereof comprises an amino acid sequence at least 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or more homologous to, or identical to the amino acid sequence forth in SEQ ID NO:1.

According to some embodiments, the wild type SlROP9 or the ortholog thereof is encoded by a polynucleotide having a nucleic acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or more homologous to, or identical to the nucleic acid sequence set forth in SEQ ID NO:2.

According to certain embodiments, the plant is homozygous for the mutant Slrop9 allele. Enhanced tolerance to drought stress has been exemplified herein with plants homozygous for the mutant Slrop9 allele.

According to certain alternative embodiments, the plant is heterozygous for the mutant Slrop9 allele.

Any mutation(s) can be inserted into the polynucleotide encoding SlROP9 or an ortholog thereof, including deletions, insertions, site specific mutations including nucleotide substitution and the like, as long as the mutation(s) result in down-regulation of the gene expression or in the production of less-functional or non-functional protein. Any method for mutagenesis as is known in the art can be used according to the teachings of the present invention including chemical mutagenesis, radio-mutagenesis and site directed mutagenesis, for example using genome editing techniques. According to certain currently exemplary embodiments, the plants of the present invention are produced by inserting a mutation within the SlROP9 gene using the CRISPR/Cas system, a CRISPR/Cas homologous and CRISPR/Cas modified systems.

The CRISPR/Cas system for genome editing contains two distinct components: a gRNA (guide RNA) and an endonuclease e.g., Cas9.

The gRNA is typically a 20-nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Comparable with other genome editing nucleases, Zinc-finger nucleases (ZFNs) and transcription activator-like effector nucleases (TALENs), the double-stranded brakes produced by CRISPR/Cas can undergo homologous recombination or nonhomologous end-joining (NHEJ).

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present bi-allelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or homology directed repair (HDR) depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are number of publicly available tools to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids.

According to certain additional or alternative embodiments, expression of the polynucleotide is affected at the genomic and/or the transcript level using a variety of molecules that interfere with transcription and/or translation (e.g., antisense, siRNA, Ribozyme, or DNAzyme) of the polynucleotide.

According to certain embodiments, the plants of the present invention are transgenic plants. According to these embodiments, the at least one modified cell comprises silencing molecule targeted to SlROP9 or to an ortholog thereof is selected from the group consisting of RNA interference (RNAi) molecule and antisense molecule.

Typically, RNA interference (RNAi) refers to the process of sequence-specific post transcriptional gene silencing mediated by small interfering RNAs (siRNA). Long double stranded RNA (dsRNA) in cells typically stimulates the activity of a ribonuclease III enzyme referred to as Dicer. The Dicer is involved in the processing of the long dsRNA into short pieces of siRNA. siRNAs derived from Dicer activity are typically about 21-23 nucleotides in length and include duplexes of about 19 base pairs.

The RNAi response also features an endonuclease complex containing siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex. According to certain embodiments, the RNAi molecule is selected from the group consisting of microRNA (miRNA), small interfering RNA (siRNA), short-temporal RNA (stRNA), double-stranded RNA (dsRNA), and short-hairpin RNA (shRNA).

Methods for transforming a plant cells with a nucleic acid sequence of a silencing molecule are known in the art. As used herein the term "transformation" or "transforming" describes a process by which a foreign nucleic acid sequence, such as a vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to typical embodiments the nucleic acid sequences of the present invention are stably transformed into a plant cell.

There are various methods of introducing foreign nucleic acid sequences into both monocotyledonous and dicotyledonous plants (for example, Potrykus I. 1991. Annu Rev Plant Physiol Plant Mol Biol 42:205-225; Shimamoto K. et al., 1989. Nature 338:274-276).

The principal methods of the stable integration of exogenous DNA into plant genomic DNA includes two main approaches:

*Agrobacterium*-mediated gene transfer: The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch et al., 1988. Plant Molecular Biology Manual A5, 1-9, Kluwer Academic Publishers, Dordrecht). A supplementary approach employs the *Agrobacterium* delivery system in combination with vacuum infiltration. *Agrobacterium* mediated transformation protocols for wheat are known to a person skilled in the art. High efficiency wheat transformation mediated by *Agrobacterium tumefaciens* is described by Ishida et al. (Ishida Y., et al. In: Ogihara Y., Takumi S., Handa H. (Eds.) Advances in Wheat Genetics: From Genome to Field. Springer, Tokyo. DOI 10.1007/978-4-431-55675-6_18).

Direct nucleic acid transfer: There are various methods of direct nucleic acid transfer into plant cells. In electroporation, protoplasts are briefly exposed to a strong electric field, opening up mini-pores to allow DNA to enter. In microinjection, the nucleic acid is mechanically injected directly into the cells using micropipettes. In microparticle bombardment, the nucleic acid is adsorbed on microprojectiles such as magnesium sulfate crystals or tungsten particles, and the microprojectiles are physically accelerated into cells or plant tissues. Another method for introducing nucleic acids to plants is via the sonication of target cells. Alternatively, liposome or spheroplast fusion has been used to introduce expression vectors into plants.

Following transformation, expression of the above described selectable marker genes allows for preferential selection of transformed cells, tissues and/or plants, using regeneration and selection methods now well known in the art.

According to certain embodiments, the plant is selected from the group consisting of a field crop plant, a cereal plant, an ornamental plant, a forest tree, a forest shrub and a leafy plant. According to certain embodiments, the plant is a cereal plant. According to some embodiments, the cereal plant is selected from the group consisting of wheat, barley, sorghum, maize, rice, oat, and rye. Each possibility represents a separate embodiment of the present invention. According to other embodiments, the plant is a field-crop plant. According to some embodiments, the field crop plant is selected from the group consisting of tomato, potato, sweet potato, cassava, beets, ginger, horseradish, radish, ginseng, turnip, any root or tuber crop, pepper, eggplant, ground cherry, tomatillo, okra, other fruiting vegetables, cucumber cantaloupe, melon, muskmelon, squash, watermelon and other cucurbit plants. According to certain additional embodiments, the plant is a crop plant grown for leafy produce selected from the group consisting of lettuce, spinach, swisschard (mangold), Medicago (medick/burclover), basil, oregano, tobacco, and cannabis.

According to certain exemplary embodiments, the crop plant is of the family Solanaceae.

According to certain exemplary embodiments, the crop plant is selected from the group consisting of tomato (*Solanum lycopersicum*), eggplant (*Solanum melongena*), potato (*Solanum tuberosum*) and tobacco (*Nicotiana tabacum*). According to certain currently preferred embodiments, the crop plant is tomato plant.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Sequence Analysis and Phylogeny

Sequences of *Arabidopsis* ROPs were obtained from TAIR (The *Arabidopsis* Information Resource (arabidopsis.org/) and SlROP9 orthologs were obtained using BLAST in Sol Genomics (solgenomics.net/) and UniProt (uniprot.org) databases. Sequences were aligned using MAFFT (mafft.cbrc.jp/alignment/software/) with default settings. ProtTest (github.com/ddarriba/prottest3) was executed to select the best fitted model for each alignment out of all available protein models. The selected models, LG+G model for the gene phylogeny and JTT+G for the species phylogeny were selected unanimously by the AIC, AICc, and BIC criteria. Finally, the phylogeny was inferred using a maximum likelihood optimization of the tree and model parameters in PhyML (atgc-montpellier.fr/phyml).

All vectors used in the current examples are described in Table 1.

TABLE 1

Vectors

| Name | Description | E. coli | Agrobacterium tumefaciens | Plant | Source |
|---|---|---|---|---|---|
| Gateway vectors | | | | | |
|  | pENTRp4-p1R-35S | Kan | | | Internal stocks |
|  | pENTR221-GFP | Kan | | | Internal stocks |
| pSYSl02 | pENTRp2rp3-SlROP9 | Kan | | | This work |
|  | pk7m34GW | Kan | | | Internal stocks |
| pSYSl10 | pk7-35S -GFP-SlROP9 | Spec | Spec + Gent | Kan | This work |
|  | pENTR221-YN | Kan | | | Internal stocks |
|  | pENTRp2rp3-YC | Kan | | | Internal stocks |
| pSYSl07 | pk7-35S-YN-SlROP9 | Spec | Spec + Gent | Kan | This work |
| pSYSl28 | pENTR221-SlICR1 without stop codon | Kan | | | This work |
| pSYSl29 | pENTR221-SlICR2 without stop codon | Kan | | | This work |
| pSYSl30 | pk7-35S-SlICR1-YC | Spec | Spec + Gent | Kan | This work |
| pSYSl31 | pk7-35S-SlICR2-YC | Spec | Spec + Gent | Kan | This work |
|  | pk7-35S-AtICR1-YC | Spec | Spec + Gent | Kan | Internal stocks |
| Plasmids for CRISPR-cas9 | | | | | |
|  | pICH86966 (SgRNA backbone) | | | | Addgene |
|  | pICSL01009 (AtU6 promoter) | | | | Addgene |
|  | pICH47751 (Carb back bone) | | | | Addgene |
| pSYSl44 | SlROP9 SgRNA-1 level-1 | | | | This work |
| pSYSl45 | SlROP9 SgRNA-2 level-1 | | | | This work |
|  | pAGM4723 | | Kan | | Addgene |
|  | pICH47732 (NPTII) | | | Kan | Addgene |
|  | pICH47742 (Cas9) | | | | Addgene |
|  | pICH41766 (L3E) | | | | Addgene |
| pSYSl48 | SlROP9 SgRNA-1 level-2 | | | Kan | This work |
| pSYSl49 | SlROP9 SgRNA-2 level-2 | | | Kan | This work |
| pSY3800 | pEntry P2r-P3 ICR1ΔN | Kan | | | This work |
| pSY3802 | pEntry 221 eGFP-linker | Kan | | | This work |
| pSY2503 | pDONR P4-P1R MCS:XVE | Kan | | | Siligato R, et al. Plant Physiol 170, 627-641 (2016) |
| pSY3837 | pEntry P4-P1R ROP11:XVE | Amp | | | This work |

TABLE 1-continued

| | | Vectors | | | |
|---|---|---|---|---|---|
| Name | Description | E. coli | Agrobacterium tumefaciens | Plant | Source |
| pSY3809 | pExpressionB7 pROP11-XVE-eGFP-linker-ICR1ΔN | Spec | Spec + Gent | Basta ® | This work |

Table 1: Kan—kanamycin;
Spec. stands for spectomycin;
Gent—Gentamycin;
Amp.—Ampicillin;
Basta ®—Glufosinate ((RS)-2-Amino-4-(hydroxy(methyl)phosphonoyl)butanoic acid)

All reagents used in the current examples are described in Table 2.

TABLE 2

| | Reagents | | |
|---|---|---|---|
| Product name | Application | Company name | Catalog number |
| Phusion High-Fidelity DNA Polymerase | High-fidelity PCR cloning | Thermo Scientific | F530S |
| Phire Hot Start II DNA Polymerase | High throughput PCR amplifications | Thermo Scientific | F122S |
| Phire Green Hot Start II DNA Polymerase | High throughput PCR amplifications | Thermo Scientific | F124S |
| Taq Ready Mix | Colony PCR (bacteria and yeast) | Hy-labs | EZ-3007 |
| BsaI-HF restriction enzyme | Restriction enzyme cloning | New England Biolabs | R3535 |
| BbiI/BbsI-HF restriction enzyme | Restriction enzyme cloning | New England Biolabs | R3539S |
| FastAP Thermosensitive Alkaline Phosphatase | Dephosphorylation of cloning vector to prevent recircularization during ligation | Thermo Scientific | EF0654 |
| T4 DNA Ligase | Ligation of DNA fragments generated by restriction enzymes (for difficult reactions) | NEB | M0202T |
| Gateway BP Clonase II Enzyme Mix | BP recombination reaction | Invitrogen | 11789-020 |
| Gateway LR Clonase II Plus Enzyme Mix | MultiSite LR recombination reaction | Invitrogen | 12538-120 |
| Wizard SV Gel and PCR Clean-Up System | Gel extraction of DNA fragments and purification of PCR products | Promega | A9281 |
| DNA-spin Plasmid DNA Purification Kit | Purification of bacteria plasmid DNA | iNtRON Biotechnology | 17096 |
| AccuPrep Plasmid Mini Extraction Kit | Purification of bacteria plasmid DNA | BIONEER | K-3030 |
| GenElute Plant Genomic DNA Miniprep Kit | Elicitation of plants DNA | Sigma-Aldrich | G2N70-1KT |
| RNeasy Plus Mini Kit | Elicitation of plants total RNA | QIAGEN | 74134 |
| High Capacity cDNA Reverse Transcription Kit with RNase Inhibitor | Reverse transcription of mRNA to single-stranded cDNA | Applied Biosystems | 4374966 |
| Fast SYBR Green Master mix | For q-PCR | Applied Bosystems | 4385612 |
| Abscisic acid (ABA) | Plant hormone | Sigma Aldrich | A1049 |
| 2',7'-dichlorofluorescien diacetate (H₂DCF-DA) | DCF fluorescence (for ROS) | Sigma Aldrich | D6883 |
| Diphenyleneiodonium chloride (DPI) | NADPH oxidase inhibitor | Sigma Aldrich | D2926 |
| B-estradiol | Induction of ROP activity | Induction of ROP activity | Induction of ROP activity |

All oligonucleotide primers used in the current examples are listed in Table 3.

TABLE 3

Oligonucleotide primers

| Primer name | Target gene | Sequence | Use | Reference/ SEQ ID NO. |
|---|---|---|---|---|
| S1TUBULIN-F | S1Tubulin | CACATTGGTCAGGCCGGTAT | QPCR | Nir I. et al., Plant Cell 29, 3186-3197 (2017). SEQ ID NO: 13 |
| S1TUBULIN-R | S1Tubulin | ATCTGGCCATCAGGCTGAAT | QPCR | Nir I. et al., (ibid) SEQ ID NO: 14 |
| S1ROP9-F | S1ROP9 | GTGTCACGGTTGGTGATGGGG | QPCR | This work SEQ ID NO: 15 |
| S1ROP9-R | S1ROP9 | CTGCTCCTCGGTAGCTCAGTGG | QPCR | This work SEQ ID NO: 16 |
| attB2-S1ROP9 F | S1ROP9 | GGGGACAGCTTTCTTGTACAAAGTGGCCGCCTC AAGTGCTTCAAGATTCAT | cloning | This work SEQ ID NO: 17 |
| attB3-S1ROP9-R | | GGGGACAACTTTGTATAATAAAGTTGTTCACTT TAAACAAACGAGCTTCCTTCCG | Cloning | This work SEQ ID NO: 18 |
| attB1S1ICR1-F | S1ICRI | GGGGACAAGTTTGTACAAAAAAGCAGGCTTAAT GCCAAGATTAAGGGGATCAGATATGCTTCAAAG G | Cloning | This work SEQ ID NO: 19 |
| attB2S1ICR1-R | S1ICRI | GGGGACCACTTTGTACAAGAAAGCTGGGTGTTT GTGTCCCTTCTTTCTCCACAGGTATCCAAGC | Cloning | This work SEQ ID NO: 20 |
| attB1S1ICR2-F | S1ICR2 | GGGGACAAGTTTGTACAAAAAAGCAGGCTTAAT GCCAAGATCAAGGGGATCAGAAATGCC | Cloning | This work SEQ ID NO: 21 |
| attB2S1ICR2-R | S1ICR2 | GGGGACCACTTTGTACAAGAAAGCTGGGTGTTT GTGGCCCTTCTTCTTCCAGAGGTCACC | Cloning | This work SEQ ID NO: 22 |
| SGRNA-1-F | S1ROP9 (exon3) | tgtggtctcaATTGCACCGTCGGAACATAGTCC gttttagagctagaaatagcaag | CRISPR | This work SEQ ID NO: 23 |
| SGRNA-2-F | S1ROP9 (exon 5) | tgtggtctcaATTGCTAATACCACCGGAATTCC gttttagagctagaaatagcaag | CRISPR | This work SEQ ID NO: 24 |
| SYP 2570 | S1ROP9-R | tgtggtctcaAGCGTAATGCCAACTTTGTAC | CRISPR | This work SEQ ID NO: 25 |
| SYP 3826 | ICR1-R | GATCCATGAACCCAGCTGACGG | Cloning | This work SEQ ID NO: 26 |
| SYP 3827 | eGFP-F | CTACCTGAGCACCCAGTCCG | Cloning | This work SEQ ID NO: 27 |

TABLE 3-continued

Oligonucleotide primers

| Primer name | Target gene | Sequence | Use | Reference/ SEQ ID NO. |
|---|---|---|---|---|
| SYP 3830 | eGFP-R | GTCGCCGTCCAGCTCGAC | Cloning | This work SEQ ID NO: 28 |
| SYP 2508 | XVE-F | CGGGGGAGGCAGAGGGTTTCC | Cloning | Cloning SEQ ID NO: 29 |

Table 3: "R"—Reverse; "F"—Forward

Plant line used in the current examples are listed in Table 4.

TABLE 4

Plant lines

| Species | Name | Genotype | Source |
|---|---|---|---|
| Tomato (S. lycopersicum) | S. Lycopersicum cv M82 | | |
| Tomato (S. lycopersicum) | Slrop9-1 | InDel in exon 3 of SlROP | This work |
| Tomato (S. lycopersicum) | Slrop9-2 | InDel in exon 3 of SlROP | This work |
| Tomato (S. lycopersicum) | Slrop9-3 | InDel in exon 5 of SlROP | This work |
| Tomato (S. lycopersicum) | Slrop9-4 | InDel in exon 5 of SlROP | This work |
| Arabidopsis | ROP probe #5-4 | pROP11:XVE-eGFP-linker-ICR1ΔN | This work |
| Arabidopsis | ROP probe #8-4 | pROP11:XVE-eGFP-linker-ICR1ΔN | This work |

Quantitative PCR (QPCR)

Tissue-specific expression of SlROP9 was verified by QPCR. Total RNA was extracted from roots, stems, and cotyledons of 8-day-old seedlings grown on 0.5× Murashige Skoog (MS)+1% agar and from young leaves, mature leaves (fully expanded leaflets next to flag leaflet from $2^{nd}$ or $3^{rd}$ compound leaf), flower buds, anthers, gynoecia (both from open flowers), and young developing fruits (5-8 cm) using the RNeasy Plant Mini Kit (Qiagen). cDNA prepared using a High-capacity cDNA Reverse Transcription Kit (Applied Biosystems). Fast SYBR green used for QPCR on Step One Plus Real-time PCR (Applied Biosystems). Mean (±SE) ΔCT values of three biological replicates (normalized to tubulin for each sample) were used in graph preparation. The following oligonucleotide primers were used: tubulin-F, tubulin-R, Slrop9-F and SlROP9-R (Table 3).

For expression of ABA induced genes, total RNA was extracted from mock-treated or ABA-treated cotyledons or from 2- to 3-week-old soil-grown plants using the RNeasy Plant Mini Kit (Qiagen). cDNAs were prepared using the High-capacity cDNA Reverse Transcription Kit (Applied Biosystems). Oligonucleotide primers for tubulin, P5CS1, and RAB18 were identical to those used by Nir et al. (2017, ibid). Expression was normalized to tubulin. Gene expression of the M82 mock-treated samples was set to 1, and then remaining samples were calculated proportionately. Data are the means (±SE) of three independent biological replicates.

Molecular Cloning

For expression of GFP-ROP9, destination vectors were prepared with the Invitrogen Multisite Gateway Three-fragment Vector Construction Kit. Total RNA was extracted from young stems of 10-day-old tomato seedlings grown on 0.5×MS using an RNeasy Plant Mini Kit (Qiagen). cDNAs were prepared using the High-capacity cDNA Reverse Transcription Kit (Applied Biosystems). The SlROP9 CDS was amplified with attB2-SlROP9 F and attB3-SlROP9-R designed with attB2 and attB3 flanking regions using SnapGene 4.3.10 and fused in to pDONR-P2RP3 using the BP Clonase reaction. The GFP-tag cloned into pDONR-221, the cauliflower mosaic virus 35S promoter cloned into pDONR-P4P1R, and pENTR carrying SlROP9 were assembled into pDEST R4-R3 vector pK7m34GW. SlICR1 and SlICR2 were subcloned into a BiFC YC vector using Three-way GATEWAY, as described above using the following oligonucleotide primer pairs: attB1SlICR1-F and attB2SlICR1-R for SlICR1 and attB1SlICR2-F and attB2SlICR2-R for SlICR2. Cloning procedures were conducted using the Gateway® recombinational cloning. pDONR P4-P1R MCS: XVE (pSY2503) (Siligato R, et al. Plant Physiol 170, 627-641. 2016) was used to for cloning the GFP-Linker-ICR1ΔN under estradiol inducible ROP11 promoter. The linker between the GFP and ICR1ΔN consisted of three repeats of $Gly_4Ser_1$ (3×GGGGS).

Transient Expression Assay

The pDEST vectors were transformed into *Nicotiana benthamiana* abaxial epidermis by infiltration through *Agrobacterium tumefaciens* GV3101. Expression was visualized 48 h post transformation using a Zeiss LSM 780 NLO confocal microscope with excitation and emission at 488 nm and at 515 nm, respectively.

Bimolecular Fluorescence Complementation (BiFC) Assays

The interaction of SlROP9 with ICRs was verified by BiFC assays as previously described (Bracha-Drori K, et al. Plant J 40, 419-427. 2004). SlROP9 was fused to YN and the ICRs were fused to YC. *A. tumefaciens* GV3101 carrying destination vectors were infiltrated in equal proportion to *N. benthamiana* abaxial epidermis. YFP reconstitution was visualized 48 h post transformation with a Zeiss LSM 780 NLO confocal microscope with excitation and emission at 514 nm and 527 nm, respectively.

CRISPR/Cas9 Mutagenesis of SlROP9

Target sequences for sgRNA preparation were designed using the algorithm available at cbi.hzau.edu.cn/crispr/and verified using the algorithm available at genome.arizona.edu/crispr/. Two sgRNAs prepared for SlROP9 in exons 3 and 5 with 5'-tgtggtctcaAT-TGNNNNNNNNNNNNNNNNNNNNgttt-tagagctagaaatagcaag-3' (SEQ ID NO: 30) as a backbone and F primers prepared with the following 20 nucleotides and the PAM sequence. Assembly of destination vectors was carried out essentially as previously described (Belhaj, K. et al., Plant methods 9, 39, 2013; Hopes A. et al., bio Protocol 7, e2625, 2017). Two sgRNAs were amplified with SGRNA-1-F and SYP2570 or with SGRNA2-F and SYP2570 primers using pICH86966 carrying the sgRNA backbone with the AtU6 promoter as a template. The PCR reaction was carried out with high-fidelity DNA polymerase (Thermo Scientific Phusion) with annealing temperature of 60° C. and 10-s elongation for 30 cycles. PCR products were purified and assembled with pICSL01009 (AtU6 promoter) and pICH47751 (Carb) to generate the level-1 vector (AtU6p: SgRNA) after cleavage with BsaI and ligation with T4 Ligase (NEB M0202T). The level-1 vector carrying pICH4775: AtU6: SgRNA was assembled with other level-1 vectors carrying pAGM4723 (Kan), pICH47732 (NPTII), pICH47742 (Cas9), and pICH41766 (L3E) to generate level-2 vectors after cleavage with BbiI and ligation with T4 Ligase.

Level-2 plasmids were transformed into tomato cotyledons using *A. tumefaciens* LBA4404 and TO plants regenerated through tissue culture on kanamycin (McCormick et al., Plant Cell Rep 5, 81-84, 1986). Total genomic DNA was extracted from 2 or 3 leaflets from different branches of TO plants using Gen Elute Plant Genomic DNA Mini Prep Kit. Primers were prepared for amplification of sgRNA target sites with 406 bp and 542 bp flanking sgRNA1 and sgRNA2 PAM regions, respectively. PAM regions were amplified using Phusion High-fidelity DNA Polymerase, and PCR products were purified and sequenced with F and R primers to select mutant plants. Seeds of TO heterozygotes were sown to produce Tl plants, which were double screened for both segregations out of the Cas9 T-DNA and presence of homozygous mutations.

*Arabidopsis* Transformation and Selection.

*Arabidopsis* Col-0 plants were transformed using the floral dip method (Clough SJ, et al. Plant J 16, 735-743, 1998). Transgenic plants were selected with Basta. All Analysis was carried out on homozygous non-segregating plants using two independent transgenic lines.

Estradiol Induction and ABA Treatment of *Arabidopsis*

Expression of GFP-ICR1ΔN was induced in 7-days old *Arabidopsis* seedlings with 5 μM β-estradiol dissolved in 99.5% DMSO. After 24 h of induction plants were treated with control (0.5× Murashige Skoog (MS) medium supplemented with 0.1% ETOH (control) or with 10 μM ABA dissolved in 0.1% ETOH. Analysis of GFP-ICR1ΔN distribution was carried out 1 h after treatments with control or ABA supplemented media using Zeiss LSM 780-NLO confocal microscope by excitation at 488 nm and emission spectrum at 501-546 nm using 40× and 63× water objectives. Image analyses were performed with ZEN 2012 Digital Imaging and Image J.

Phenotypic Analyses

Analyses were performed with 4-week-old plants (3 weeks after germination) grown on Soilrite mix in a greenhouse at 25 (±2° C.) open to daylight. M82 and rop9 mutant plants were equally irrigated in the same tray before the beginning of experiments. Control plants were watered on alternate days and photographed 12 h after irrigation. For drought experiments, photos were taken 3 days and 7 days after irrigation. Photos were taken with a Canon EOS 400D digital camera. Experiments were repeated three times with three plants for each genotype.

RGB Color Indexing

RGB color indices in the olive-green range for 2-week-old plants (one week after germination) were determined using the Plant Phenomics Photon System Instruments.

Infrared Thermal Imaging

Thermal imaging was carried out with FLIR T660 IR camera on 4-week-old plants with or without drought treatments. To visualize temperature differences, transpiration was maximized by taking photographs in the open air and under sunlight. Experiments were repeated three times. Images were analyzed by FLIR-Tools (flir.com/products/flir-tools/).

Gas Exchange and Photosynthesis Measurements

Stomata conductance, transpiration rates, and $CO_2$ assimilation were measured with LICOR6400XT on 4-week-old greenhouse-grown plants (13 h light/11 h dark cycles, temperature 25° C.). Photosynthesis was induced at 500 μmol photons $m^{-2}$ $s^{-1}$ with 10% blue light. $CO_2$ surrounding the leaf was set to 400 μmol $mol^{-1}$ $CO_2$, and temperature was set to 25° C. To minimize variation, all the measurements were carried out in a specified area in the greenhouse between 9:30 AM and 13 PM. Measurements were carried out on six plants from each genotype and on two fully expanded leaflets from each plant. Measurements were carried out on 4 consecutive days on control plants (irrigated 12 h before measurements) or following 2, 3, or 4 days of drought. The presented measurements are of plants after 3 days of drought or the control plants. Experiments were repeated at least twice.

Stomata Distribution

Cotyledons were affixed to glass slides with Telesis 5 silicone adhesive (Premiere Products) at abaxial or adaxial epidermis. To isolate the epidermis, the other tissues were carefully removed with a cover glass. Tissues were washed and bright-field images were taken with a Zeiss-LSM 780 NLO confocal microscope using a bright-field detector and a 20× water lens. To cover all areas of cotyledon, six to seven different regions were imaged. Stomata were counted in 1 $mm^2$ areas.

Seed Germination Assays

Seeds of M82 and rop9 mutant plants (50 seeds per genotype) were surface sterilized for 2 min in ethanol followed by 20 min in 3% sodium hypochlorite, washed with excess of water (~100 ml) and sown on 0.5×MS+1% agar plates (without sucrose) supplemented with 0.1% ethanol (mock) or 1 or 5 μM ABA (in 0.1% ethanol). Seeds were kept at 4° C. for 48 h for scarification and moved to 25° C. in the dark for germination. The percentage of seeds germinated were determined after seven days.

Primary Root Elongation Assays

Seven-day-old M82 and rop9 mutant seedlings were transferred to 0.5×MS+1% agar plates (without sucrose) supplemented with 0.1% ethanol (mock) or 1 or 5 μM ABA in 0.1% ethanol, and root lengths were marked. Root elongation was measured after 48 h.

Measurements of Stomata Aperture

Double-blind assays were carried out as previously described (Puli, M. R. et al., J Exp Bot 63, 1349-1356, 2012). with the following modifications. Cotyledons were excised from M82 or rop9 mutants (10-15 days after sowing in soil) and were transferred immediately to stomatal opening buffer (10 mM MES-KOH, pH 7.0, 50 mM KCl) with or without ABA and treated for 3 h under light (110 to 120 μE $m^{-2}$ $s^{-1}$). Mock-treated controls were treated with 0.1% vol/vol ethanol. After 3 h, the abaxial epidermis of cotyledons was affixed to a glass slide with Telesis 5 silicone adhesive (Premiere Products) and bright-field images were taken with a Zeiss-LSM 780 NLO confocal microscope. For each biological replicate, width and length of 30 to 40 stomatal apertures were measured using Image J.

ROS Measurements

Reactive oxygen species (ROS) levels in guard cells were monitored using a fluorescence-based assay with 2',7'-dichlorofluorescien diacetate ($H_2DCF$-DA). Abaxial epidermises of cotyledons were mounted on microscope slides with medical adhesive Telesis V and loaded with stomatal opening buffer with 50 µM $H_2DCF$-DA for 30 min. Excess $H_2DCF$-DA was removed by washing with water, and samples were loaded with 0.1% ethanol (mock) or 10 µM ABA in opening buffer. After 15 min, fluorescence images were collected using a Zeiss-LSM 780 NLO confocal microscope. Fluorescence measured from about thirty stomata of each biological replicate was determined using Image J.

Whole Plant Physiological Performance

Whole-plant physiological performance was monitored with the functional phenotyping system Plantarray platform (Halperin O, et al. Plant J 89, 839-850, 2017). The experiment was performed during January 2020 in minimally controlled greenhouses. The experimental setup was followed as described in Dalal et al. (Dalal A, et al. Front Plant Sci 10, 905. 2019; Dalal A, et al. bioRxiv, 2020). Briefly, the Plantarray system was calibrated before the experiment start, and 4-L pot was used with potting soil (Tuff Marom Golan, Israel) as the growing media. The seeds were germinated and grown on side tables inside the same greenhouse for 3 weeks before they were transferred into the pots. After 3 more weeks in the pots plants were measured. The conditions in the greenhouse were light (9-851 µmol m$^{-2}$ s$^{-1}$); temperature (7-21° C.) and relative humidity (RH) (30.6-96.3%) as monitored by the Plantarray meteorological station (Plant-Ditech Ltd., Israel). The nutrients composition supplied to the plants by the automated irrigation system (fertigation) was as described in Dalal et al. (2019, ibid). The analysis was carried out for 5 constitutive days before the experiment was terminated. The VPD and Transpiration Rate (TR) of the plants during the course of the experiment were determined and calculated using previously described protocols (Dalal et al. 2019, 2020, ibid) and the equations implemented in the SPAC-analytics software. The VPD and TR were retrieved from the software and the later was used to calculate the E (TR normalized to the fresh shoot weight). The fresh shoot was harvested at the end of the experiment.

Statistical Analyses

Sample sizes are as specified in figure legends and/or the Materials and Methods. Quantifications and calculations were carried out with Microsoft Excel and JMP (SAS Institute). Statistical variance was calculated by comparing means using a one-way ANOVA; comparisons for all pairs were performed using the Tukey-Kramer HSD.

Example 1: SlROP9 Homologs

Figure 1:
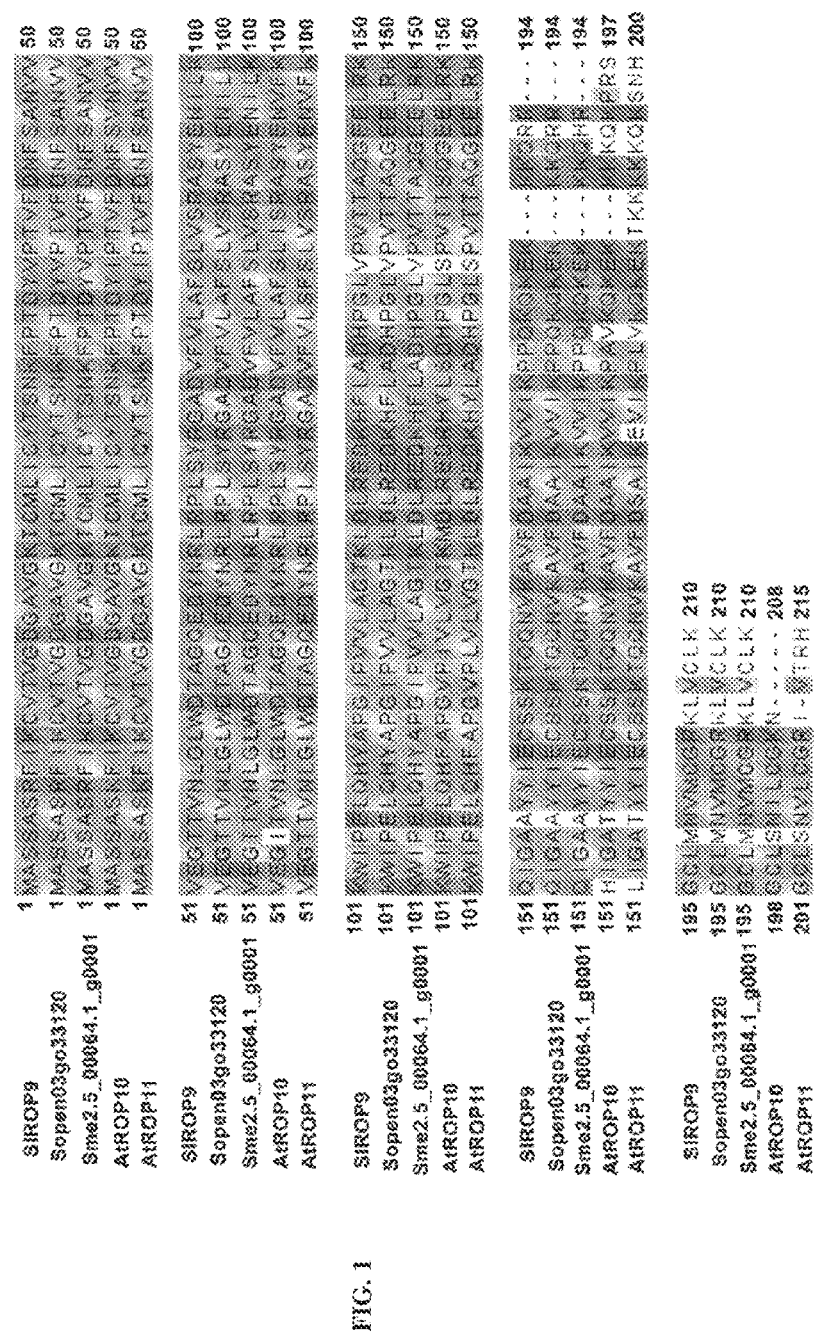

Phylogenetic analysis showed that tomato *Solanum lycopersicum* Solyc03114070.3, designated SlROP9 (ROP9) is the single homolog of *Arabidopsis* AtROP10 and AtROP11. Tomato is a crop plant regularly grown in the greenhouse or field and is therefore highly suitable for analyzing the role of ROPs in WUE. The amino acid sequences of SlROP9 homologs in the Solanaceae, including the wild tomatoes *Solanum pennellii* and *Solanum pimpinellifolium* and the crop species eggplant (*Solanum melongena*) and potato (*Solanum tuberosum*), are over 99% conserved (FIG. 1), suggesting that their functions are likely conserved. Similar to AtROP10 and AtROP11, GFP-ROP9 localized primarily in the plasma membrane following transient expression in *Nicotiana benthamiana* leaf epidermis cells (FIG. 2A) and interacted with the *Arabidopsis* ROP effector AtICR1 (Lavy et al. 2007, Curr. Biol, 17:947-952) and its tomato homologs SlICR1 and SlICR2 as demonstrated using bimolecular fluorescence complementation (BiFC) assays (FIG. 2B). These data suggest that SlROP9 is structurally and functionally conserved.

Example 2: Production of SlROP9 Mutant Alleles

Mutants of SlRO9 were generated using CRISPR/Cas9 genome editing, using the commercial tomato variety M82 as a genetic background. Two single guide RNAs (sgRNAs) were designed that uniquely recognize sequences in the third and fifth exons of SlRO9 (FIG. 3A). These sgRNAs do not have significant complementarity to other regions of the genome and, therefore, should not have off-target effects. From plants that expressed sgRNA1, two independent mutant alleles with a single nucleotide insertion and a 4-bp deletion were identified and designated rop9-1 and rop9-2, respectively. rop9-3 and rop9-4 mutants were generated upon transformation with sgRNA2 and found to have a two-nucleotide and a single nucleotide deletion, respectively (FIGS. 3B and C). All four mutant alleles cause frameshifts and contain early stop codons that are predicted to result in truncated peptides that lack essential parts of the G-domain. These mutants are therefore likely to be loss-of-function (null) mutants (FIG. 3D). Plant homozygous for each of the mutation from which the Cas9 gene has been out-segregated were identified, verified by sequencing (FIG. 4), and used for further analysis. These plants are designated herein "rop9 mutant(s)" or "rop9 mutant plant(s)".

Example 3: Drought Tolerance of Slrop9 Mutants

Figure 3E:
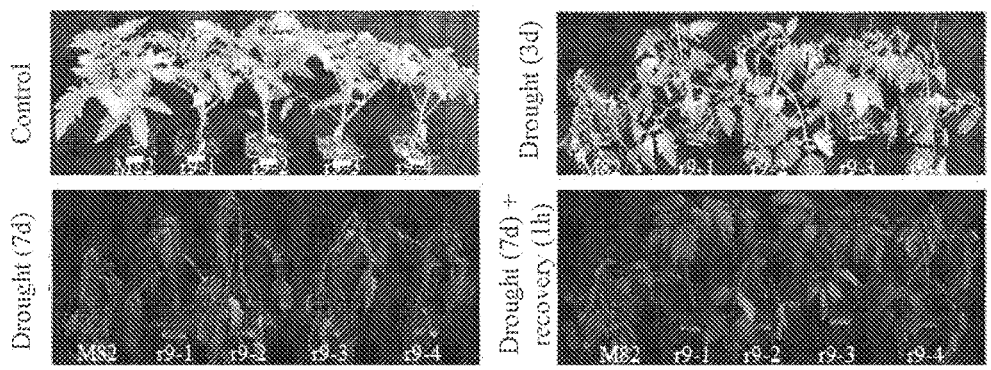
FIG. 3 demonstrates the rop9 mutants and their drought resistant phenotype.
FIG. 3A: A schematic representation of the Slrop9 locus (Solyc03g114070.2.1 SL2.50ch03 64118342 . . . 64110442) with exons indicated in gray and introns in black. The sites targeted by sgRNA1 and 2 are indicated by arrows.
FIG. 3B: Nucleotide sequences of the rop9 mutants (r9-1, SEQ ID NO:35; r9-2, SEQ ID NO:36) and the corresponding parental M82 sequence (SEQ ID NO:37)
FIG. 3C: Nucleotide sequences of the rop9 mutants (r9-3, SEQ ID NO:39; r9-4, SEQ ID NO:40) and the corresponding parental M82 sequence (SEQ ID NO:38). The sites of insertions or deletions are indicated by arrow; the regions deleted are boxed.
FIG. 3D: The predicted amino acid sequences (from amino acid 31) of the four Slrop9 mutant alleles (r9-1, SEQ ID NO:42; r9-2, SEQ ID NO:43; r9-3, SEQ ID NO:44; and r9-4, SEQ ID NO:45) and the corresponding parenteral M82 sequence (SEQ ID NO:41). The mutations generated frameshifts that resulted in missense mutations or early stop codons in the G domain. (E) Representative images of 4-week-old M82 and rop9 plants taken 12 hours after irrigation (Control), 3 days after watering (Drought (3d)), 7 days after watering (Drought (7d)), and 7 days after watering with a 1-hour recovery after watering (Drought (7d)+recovery (1 h)).
FIG. 3F: Relative weight loss of detached leaves of M82 and rop9 mutants over time. Values are averages of fourteen leaves from seven independent experiments.
FIG. 3G: Relative weight of detached leaves after 4 h ($p \leq 0.05$). Letters above the plots show statistically significant differences calculated in all assays with one-way ANOVA, Tukey-Kramer HSD. Abbreviations: r9-1, rop9-1; r9-2, rop9-2; r9-3, rop9-3; r9-4, rop9-4.

Under control conditions (i.e., watering 12 h prior to imaging) the size of the rop9 mutant plants was comparable to that of the wild-type M82 plants (FIG. 3E, control). Following 3 days without watering the M82 plants were droopy, whereas rop9 mutant plants from all four genotypes were considerably more turgid (FIG. 3E, Drought (3d)). Following 7 days without watering, the M82 and the rop9 mutants were droopy (FIG. 3E, Drought (7 days)); however, at 1 hour after re-watering all four rop9 mutants resurrected whereas M82 plants were still droopy (FIG. 3E, Drought (7 days)+recovery (1 h)). Remarkably, fruit shape, color, weight, number per plant and Brix were not significantly different between M82 plants and the rop9 mutant plants grown in a greenhouse (FIG. 5), suggesting that ROP9 could be targeted to improve plant drought tolerance.

Figure 3F:
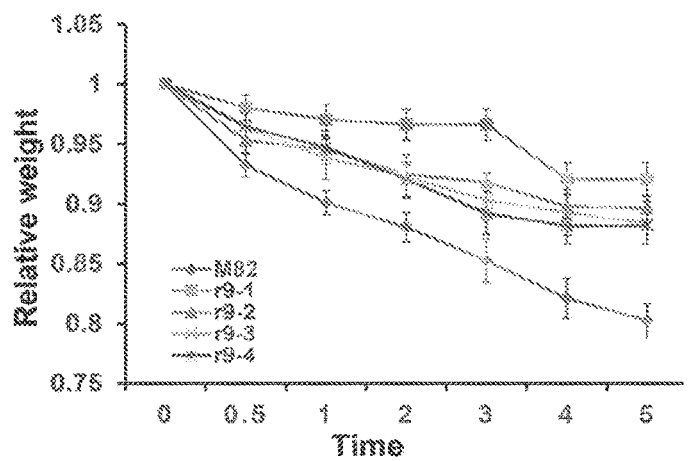
Figure 3G:
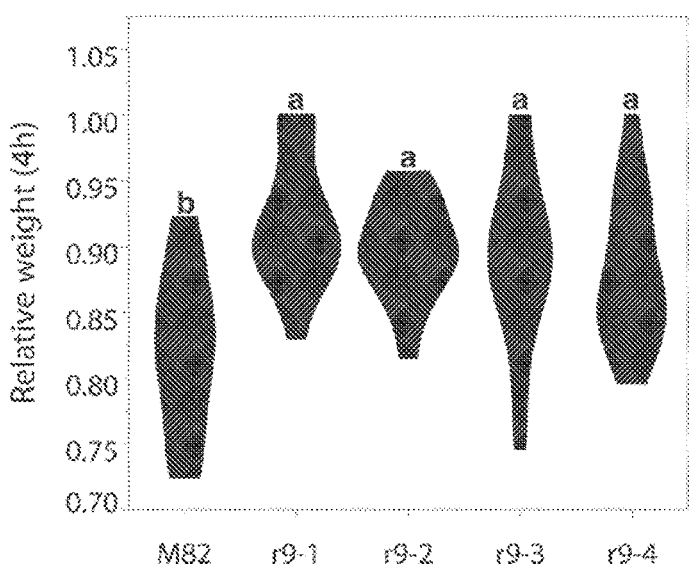
Figure 5A:
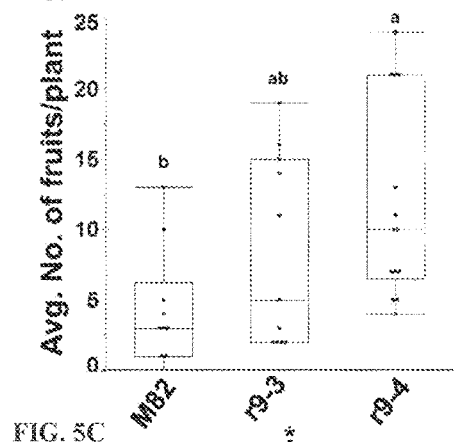
FIG. 5A: Average number of fruits per plant.
Figure 5B:
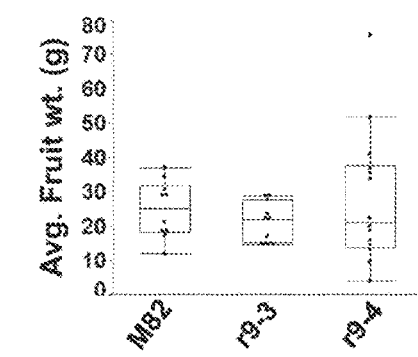
FIG. 5B: Average fruit weight in grams (g).
Figure 5C:
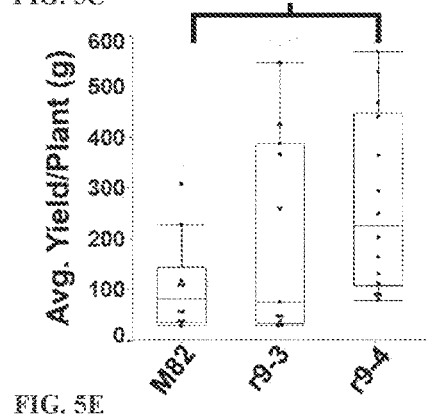
FIG. 5C: Average yield per plant in g. Calculated by multiplying fruit number and weight.
Figure 5D:
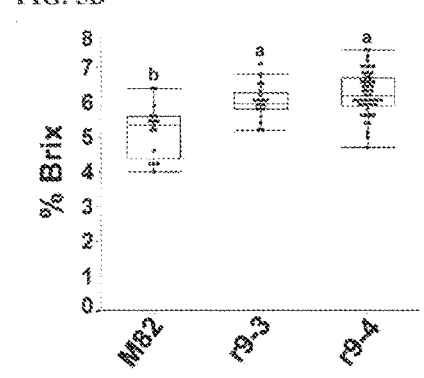
(FIG. 5D: Percent (%) Brix.
Figure 5E:
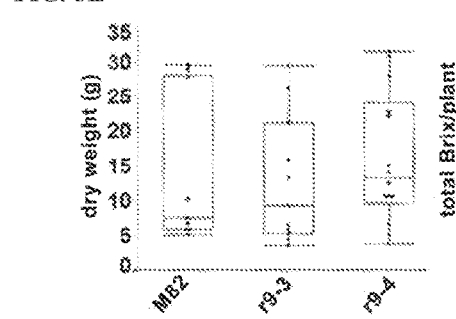
FIG. 5E: Average dry weight.
Figure 5F:
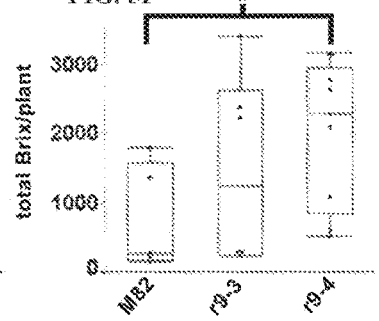
FIG. 5F: Total Brix per plant calculated by multiplying the average yield per plant with percent Brix. The boxes are interquartile range, the whiskers are the $1^{st}$ and $4^{th}$ quartiles, the line median and the black dots are all the measurements taken. n=6-14 plants per line. Statistical analysis.
Figure 6A:
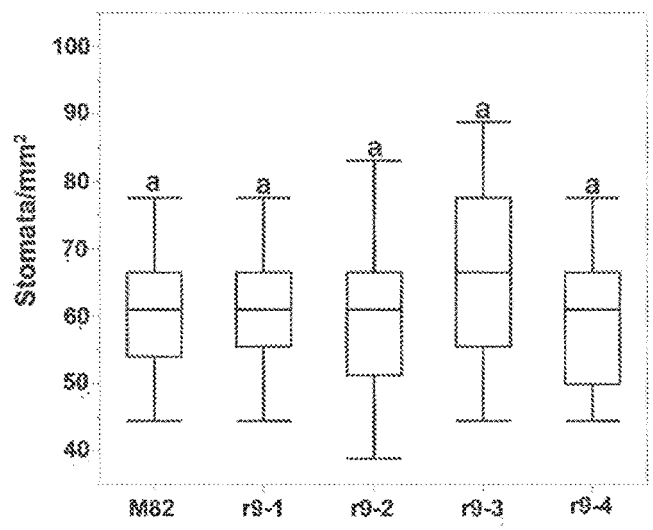
FIG. 6 shows stomatal distributions at abaxial (FIG. 6A) and adaxial (FIG. 6B) cotyledon epidermis of M82 and rop9 mutants. Values are averages of three biological replicates. Box plots represent range from upper and lower quartile, whiskers are upper and lower extreme. Letters above boxes show statistically significant differences ($p \leq 0.05$) calculated for all assays with ANOVA, Tukey Kramer HSD.
Figure 6B:
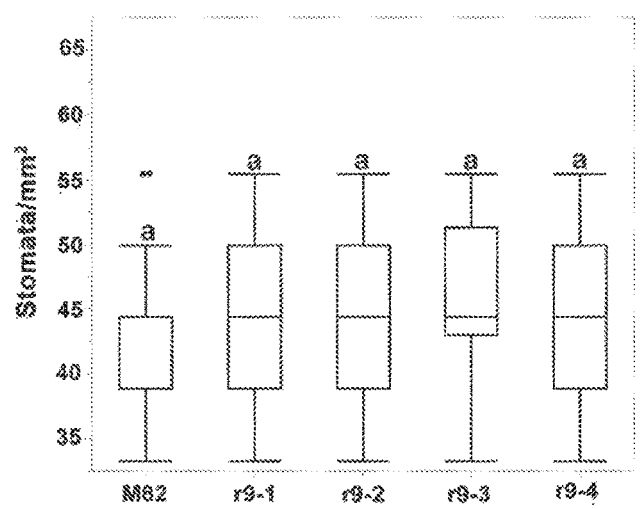
Figure 7:
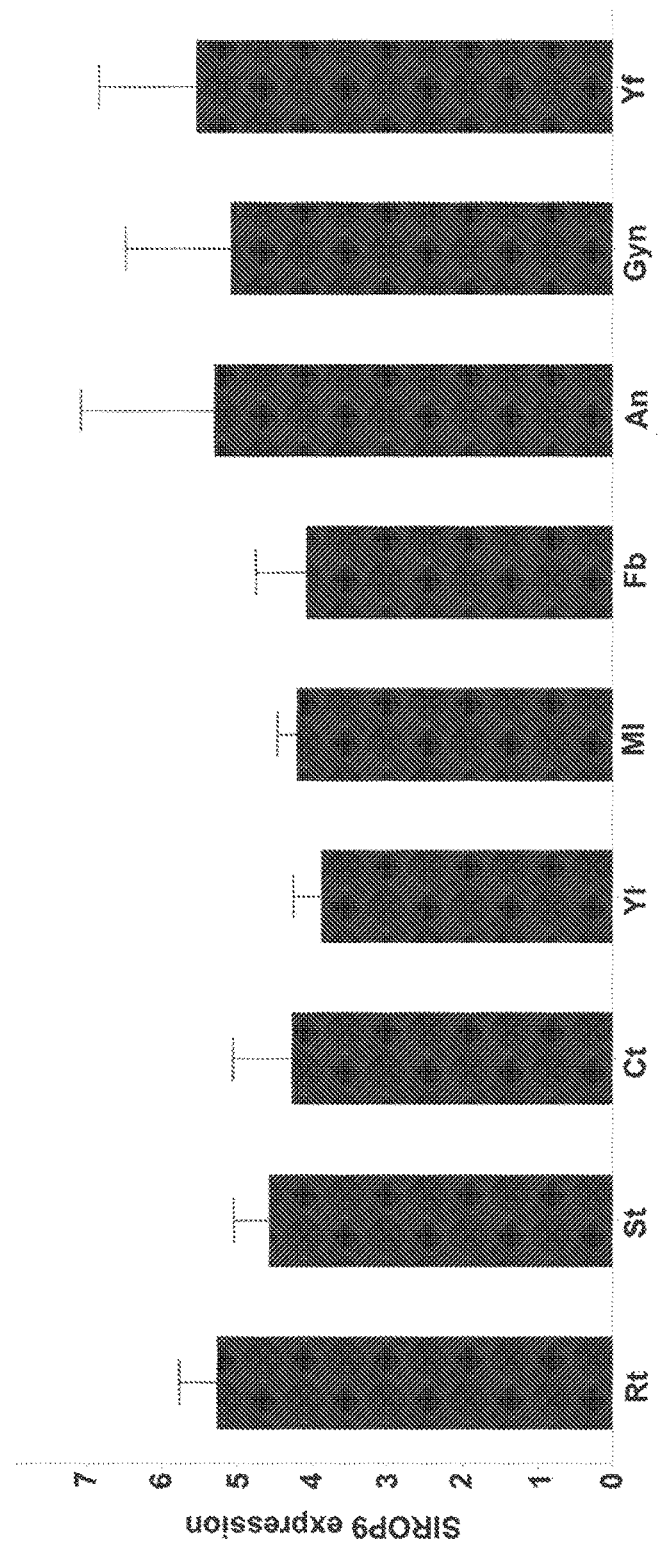
FIG. 7 shows QPCR analysis of ROP9 expression in different tissues of M82 plants. Values are means±SE (means of ΔCT mean values after normalized to tubulin) of three biological replicates collected from different plants on different days. Abbreviations: Rt, roots; St, stems; Ct, cotyledons; Yl, young leaves; Ml, mature leaves; Fb, flower buds; An, anthers; Gyn, gynoecia; and Fr, fruit.

To obtain a more quantitative measure of water loss rates, detached leaves of M82 and rop9 mutants were allowed to dry on the bench with their petioles blocked by a tape to ensure that water loss would take place primarily from the leaflet blades. Measurements of leaf weights demonstrated that the rate of water loss from the rop9 mutant leaves was reduced compared to that from M82 leaves (FIG. 3F). After 4 hours, the relative weights of the rop9 mutant leaves compared to time 0 were significantly higher than the relative weight of the M82 leaves ($p \leq 0.05$, ANOVA, Tukey-Kramer HSD) (FIG. 3G). These data suggest that the rate of transpiration from rop9 mutant leaves was reduced compared to M82. To examine whether the decreased water loss of rop9 mutants was associated with reduced stomata number, stomata densities on the abaxial and adaxial sides of cotyledons were measured. No significant differences in stomata densities between M82 and rop9 mutants could be observed (FIGS. 6A and 6B). Furthermore, gene expression analysis by QPCR demonstrated that rop9 is expressed in young and mature leaves of the M82 plants (FIG. 7). Taken together these data suggested that ROP9 regulates stomata function.

Example 4: ROP9 Function

Leaf temperature is regulated by transpiration, and transpiration rates can be assessed using thermal imaging with an infrared camera (Merlot S. et al., 2002, Plant J 30, 601-609, 2002). The leaf temperatures of irrigated rop9 mutants were higher compared than those of M82 plants (FIG. 8, control), indicating that transpiration rates of the rop9 mutants are lower than those of the wild-type plants. Remarkably, following 3 days without watering, the leaf temperatures of the rop9 mutants were lower than M82 leaf temperatures. The main temperature differences were observed in the younger leaves near the center (FIG. 8A, Drought (3d)). These data indicate that plants that do not express ROP9 maintain transpiring leaves even after 3 days of drought suggesting that the mutant plants are less affected by the drought stress than plants that express ROP9. That plants expressing four different rop9 mutant alleles generated by targeting two different regions of the gene displayed the same increased drought tolerant phenotype. This makes it extremely unlikely that the drought tolerance phenotype observed is associated with an unrelated gene, implicating SlROP9 in regulation of leaf transpiration.

Figures 8E, 8F:
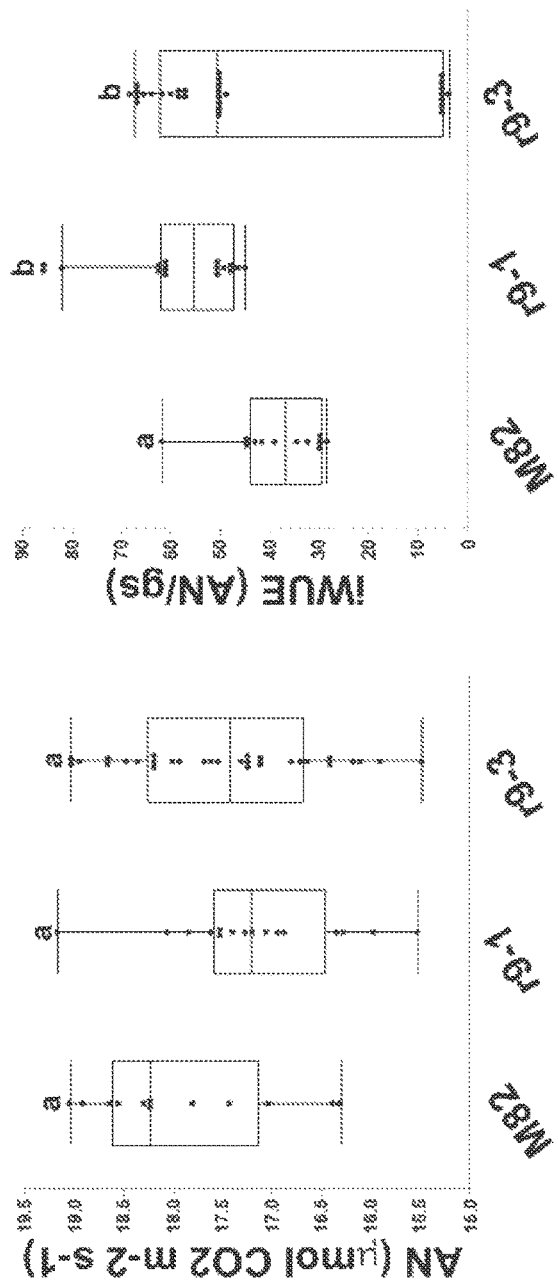

To obtain further insight into the function of ROP9 in tomato, stomata conductance, leaf transpiration rate, internal leaf $CO_2$ levels, and the rates of photosynthetic $CO_2$ assimilation were measured simultaneously using a portable LICOR6400 device. These measurements confirmed that stomata conductance and transpiration rates of rop9-1 and rop9-3 were significantly lower than those of M82 ($p \leq 0.05$, ANOVA, Tukey-Kramer HSD) (FIGS. 8B and C). The rop9-1 and rop9-3 plants also had lower intercellular $CO_2$ concentrations compared to M82 plants ($p \leq 0.05$, ANOVA, Tukey-Kramer HSD) (FIG. 8D). Remarkably, however, photosynthetic $CO_2$ assimilation rates were not significantly different between M82 WT and rop9-1 and rop9-3 mutants (FIG. 8E). Importantly, intrinsic water use efficiency, which is the ratio between the photosynthetic $CO_2$ assimilation rate and the stomata conductance, was significantly higher in the rop9 mutants than in wild-type plants ($p \leq 0.05$, ANOVA, Tukey-Kramer HSD) (FIG. 8F). Moreover, gas exchange measurements of plants following 3 days of drought demonstrated that stomata conductance and transpiration rates of rop9-1 and rop9-3 plants were significantly higher than those of M82 plants ($p \leq 0.05$ for rop9-1 and 0.01 for rop9-3, ANOVA Tukey-Kramer HSD) (FIGS. 9A and 9B).

Next, stomata aperture (width/length) was measured to examine whether the lower stomata conductance of rop9 mutants reflected enhanced stomata closure. As a positive control, it was demonstrated that treatment of M82 cotyledons with 1 or 10 µM ABA induced stomata closure ($p \leq 0.05$ ANOVA, Tukey-Kramer HSD) (FIG. 8G). The stomata apertures of rop9 mutants were significantly smaller than those of the M82 cotyledons treated under the same conditions, the mock-treated mutant apertures were of similar size to those of M82 cotyledons treated with 1 µM ABA, and those of rop9 mutants treated with 1 µM ABA resembled apertures of M82 cotyledons treated with 10 µM ABA ($p \leq 0.05$, ANOVA, Tukey-Kramer HSD) (FIG. 8G). The stomata measurements confirmed that the lower stomata conductance of the rop9 mutant is associated with smaller stomata aperture and that exogenous ABA treatment resulted in stomata closure.

Example 5: Rop9 Mutants and ABA

Results using three independent methodologies (FIGS. 8 and 9A) demonstrated that the increased drought tolerance of rop9 mutants is caused by constitutive stomata closure that results in lower stomata conductance and transpiration rates with minimal effect on photosynthetic $CO_2$ assimilation rates. Under prolonged drought, stomata conductance and transpiration from M82 leaves were reduced to a greater extent than for the rop9 mutants, likely because the wild-type plant initially loses more water and thus experiences higher drought stress, which leads to ABA-induced stomata closure. The differential response of M82 and the rop9 mutants to prolonged drought stress and the additive effects of ABA on stomata aperture size in the rop9 mutants suggest that the constitutive stomata closure of rop9 mutants is not directly related to increased ABA levels or responses.

Figure 10:
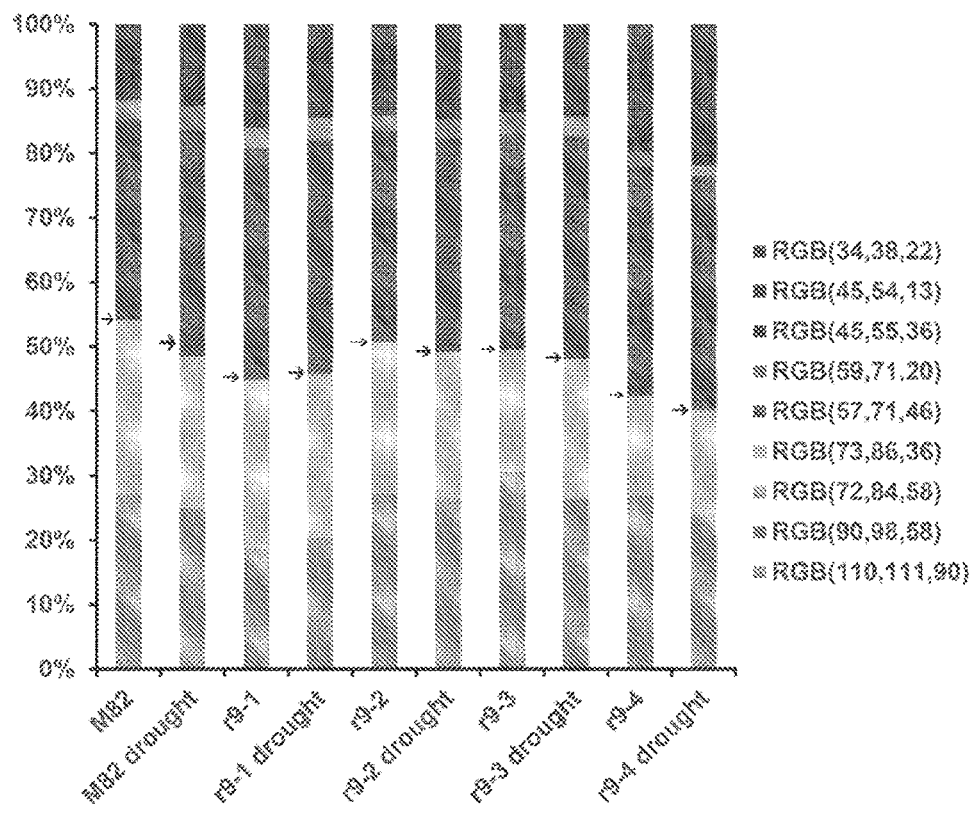
FIG. 10 shows that leaf colors of M82 and the rop9 mutants are similar. RGB color segmentation of M82 and Slrop9 mutants at olive green range under control conditions or after 3 days of drought. The regions of color changes are marked with arrows. Thinner arrows are control sets and thicker arrows are drought.

Leaf yellowing due to enhanced senescence is associated with increased levels of ABA and a more dramatic response to this hormone (Gao S. et al., Mol Plant 9, 1272-1285, 2016; Yalovsky S., et al., Plant Cell 12, 1267-1278, 2000; Zhao Y. et al., Proc Natl Acad Sci US A 113, 1949-1954, 2016). Hence, the color of leaves serves as an indication of ABA levels and the plant's response. A quantitative analysis of the green-to-yellow color patterns did not reveal increased yellowing of the rop9 mutant leaves compared to M82 leaves either from control plants irrigated 12 hours prior to analysis or from plants not watered for 3 days (FIG. 10). This lack of difference in color pattern further suggests that the drought tolerance of the rop9 mutants was not directly associated with ABA.

Figure 11E:
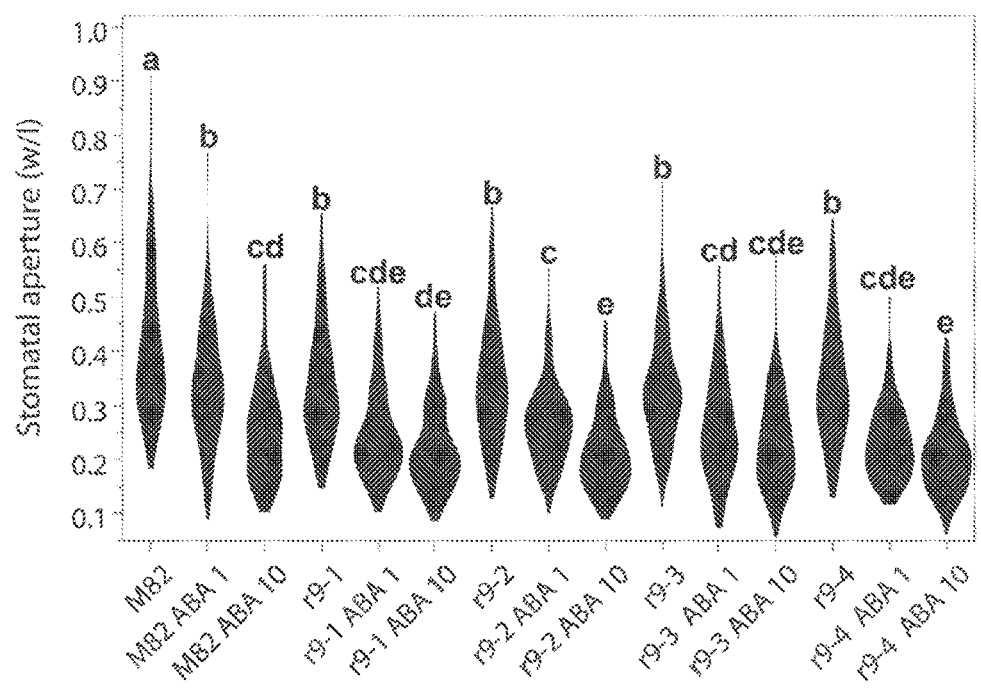
FIG. 11E: Stomata aperture (width/length) in mock-treated cotyledons (0.1% ethanol) and cotyledons treated with 1 μM ABA (ABA 1) and 10 μM ABA (ABA 10) (p≤0.05 between each increment). rop9-2 (r9-2); rop9-3 (r9-3). Letters above bars and plots note variance groups calculated in all assays with one-way ANOVA, Tukey-Kramer HSD.

Since SlrROP9 is a constitutively expressed gene (FIG. 7), seed germination and root elongation, known to be regulated by ABA, as well as ABA-induced gene expression in leaves were examined. As expected, the germination of M82 seeds was significantly inhibited by 5 µM ABA (FIG. 11A). The inhibition of seed germination in the rop9-1 mutant allele was significantly reduced compared with M82 ($p \leq 0.05$, ANOVA, Tukey-Kramer HSD). In the other three alleles inhibition of germination by ABA was reduced compared to M82; however, the differences were not statistically significant (FIG. 11A). Root elongation was inhibited to a similar extent in M82 and the rop9 mutants (FIG. 11B). It was previously shown that expression of P5CS1 and of RAB18 were upregulated by ABA in tomato mutants with increased ABA responsiveness (Nir et al., 2017, ibid). QPCR demonstrated that the levels of both P5CS1 and RAB18 in the rop9-1 and rop9-4 mutant leaves did not differ from levels in M82 leaves and that expression of these genes was induced to a similar extent by ABA in both wild-type and mutant leaves (FIGS. 11C and D). Taken together these results and the observation that during germination the rop9 mutants displayed a small ABA insensitivity strongly suggest that the smaller stomata aperture of the rop9 mutants and their drought tolerance are not directly associated with higher ABA levels or increased ABA responses. Thus, unlike mutants in *Arabidopsis* AtROP10 and AtROP11, the closest orthologs of SlROP9, the tomato rop9 mutants are not ABA hypersensitive.

Example 6: Rop9 Mutants and ROS

Figure 12A:
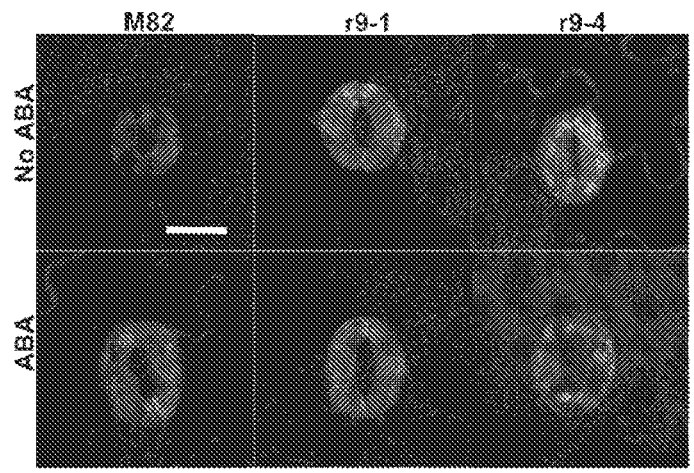
FIG. 12A: Representative images of H2DCF fluorescence in M82, rop9-1, and rop9-4 stomatal guard cells with or without ABA. Scale bar: 20 μm.
Figure 12B:
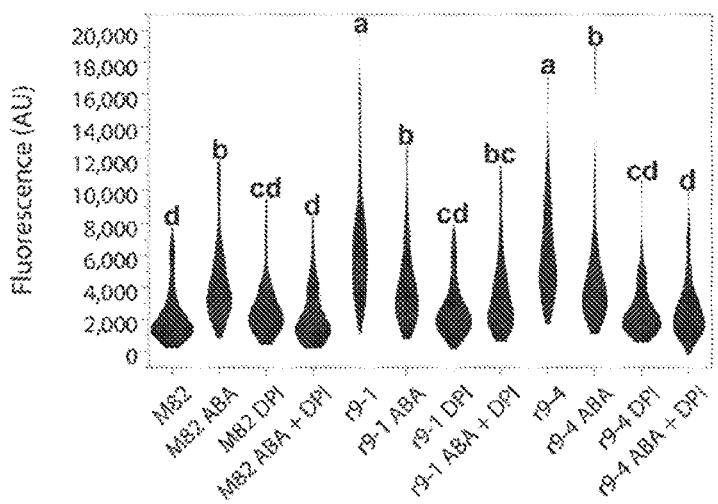
FIG. 12B: H$_2$DCF fluorescence intensities in M82, rop9-1, or rop9-4 guard cells mock-treated or treated with 10 UM ABA, 5 μM DPI, or the combination of ABA and DPI. Mock treatments: 0.1% ethanol for ABA, 1% DMSO for DPI, or both for the combination treatment. n≥90, from three biological replicates.

To explore the source of the rop9 guard cell phenotype, ROS levels were examined by labeling with the ROS fluorescent marker 2',7'-dichlorodihydrofluorescein diacetate (H2DCF-DA), which is deacetylated to form fluorescent $H_2DCF$. The rop9-1 and rop9-4 mutants guard cells had strong $H_2DCF$ fluorescence even without exogenous ABA treatments, but only basal fluorescence was observed in M82 guard cells in the absence of ABA (FIG. 12A). Signal quantification revealed that the $H_2DCF$ fluorescent intensity of the mock-treated rop9-1 and rop9-4 guard cells was significantly stronger than that of similarly treated M82 guard cells and even significantly stronger than M82 guard cells treated with 10 UM ABA ($p \leq 0.05$, ANOVA, Tukey-Kramer HSD) (FIG. 12B). Although ABA treatment induced significant enhancement in the $H_2DCF$ signal in M82 guard cells ($p \leq 0.01$, ANOVA, Tukey-Kramer HSD), these treatments significantly reduced the signal in rop9-1 and rop9-4 guard cells ($p \leq 0.05$, ANOVA, Tukey-Kramer HSD) (FIGS. 12A and B). Treatment with the NADPH oxidase specific inhibitor diphenyl iodonium (DPI) decreased the $H_2DCF$ signal in rop9-1 and rop9-4 guard cells treated with ABA to basal levels ($p \leq 0.01$, ANOVA, Tukey-Kramer HSD) (FIG. 12B), indicating that the increased ROS levels in the rop9 mutant guard cells resulted from NADPH oxidase activity.

Figure 12C:
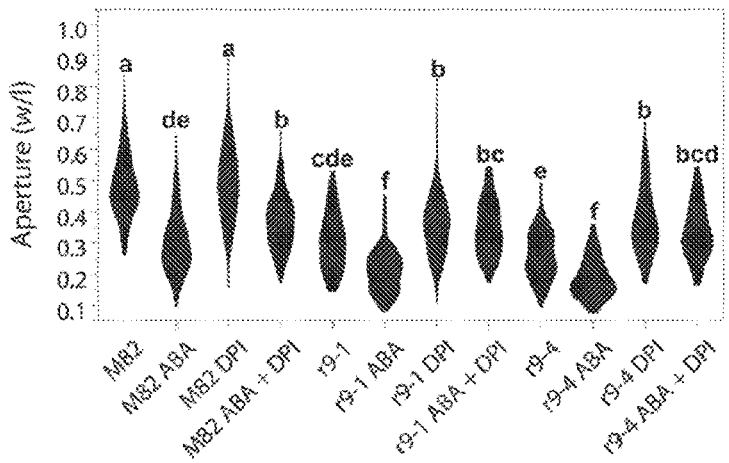
FIG. 12C: Stomatal aperture (width/length) of M82, rop9-1, and rop9-4 cotyledons mock-treated or treated with 10 μM ABA, 5 μM DPI, or both. n≥90 from three biological replicates. Letters above bars and plots are statistically significant differences calculated in all assays with one-way ANOVA, Tukey-Kramer HSD.
Figure 13:
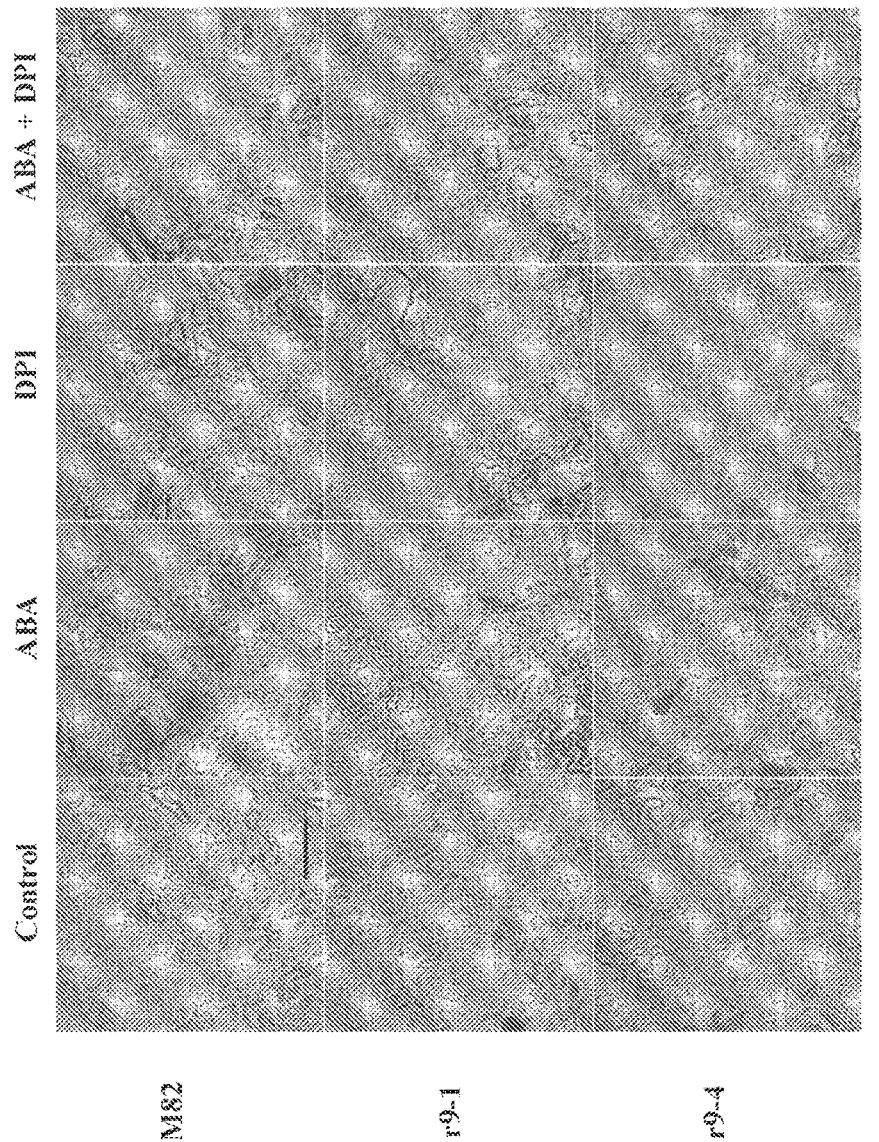
FIG. 13 shows representative images of stomatal apertures in M82, rop9-1, and rop9-4 guard cells mock-treated or supplemented with 10 μM ABA, 5 μM DPI, or both ABA and DPI. Mock treatments: 0.1% ethanol for ABA, 1% DMSO for DPI, or both for the combination treatment. Scale bar: 100.

Next, stomata apertures were measured following treatments with either or both ABA and DPI to examine the link between the constitutive RBOH-dependent ROS production in the rop9 mutants and the phenotype of the mutant guard cells. Treatment with 10 μM ABA served as positive control and expected closing of stomata were observed in M82, rop9-1, and rop9-4 cells (FIGS. 12C and 13). DPI had no effect on M82 stomata but induced opening of rop9-1 and rop9-4 stomata ($p \leq 0.05$-$0.01$ for rop9-1, $p \leq 0.001$ for rop9-4, ANOVA, Tukey-Kramer HSD), and co-treatments with ABA and DPI repressed the additive effect of ABA on the rop9 mutants guard cell apertures (FIGS. 12C and 13). The guard cell apertures of rop9-1 and rop9-4 mutants treated with the combination of ABA and DPI were significantly larger than those treated only with ABA ($p \leq 0.001$, ANOVA Tukey-Kramer HSD) and not significantly different from guard cells that were treated with DPI alone (FIGS. 12C and 13). For M82 apertures, the combined ABA and DPI treatment caused partial opening of the stomata aperture compared to treatment with ABA alone ($p \leq 0.01$, ANOVA, Tukey-Kramer HSD), but the aperture was still smaller compared to mock-treated or DPI-treated guard cell ($p \leq 0.05$, ANOVA, Tukey-Kramer HSD) (FIGS. 12C and 13). Although the DPI treatments did not induce complete recovery of stomata aperture sizes in the rop9 mutants to wild-type levels, as might be expected with inhibitor treatments, these data are indicative of a link between constitutively high ROS levels, NADPH oxidase activity, and the abnormally small stomata aperture in rop9 mutants. The results also confirm the additive nature of rop9 loss of function and ABA on guard cell aperture size.

Figure 16A:
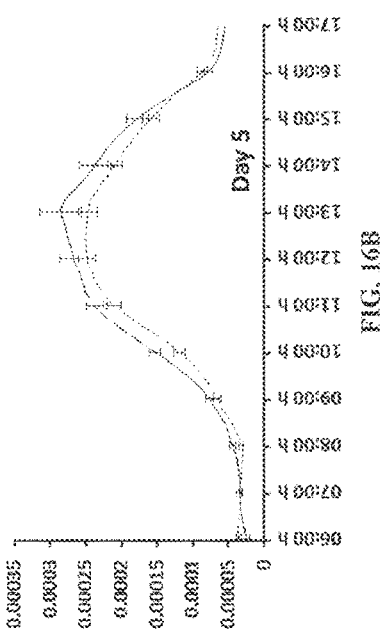
FIGS. 16A and 16B: Mean±SE diurnal E (normalized transpiration rate) from 0600 to 1700 h during day 3 and day 5 respectively.
Figure 16B:
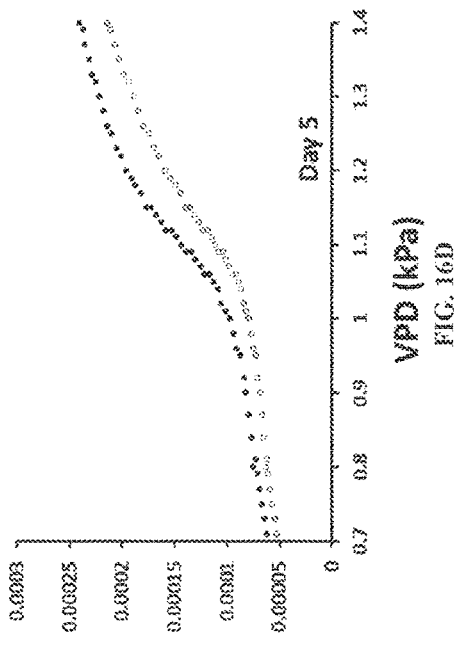
Figure 16C:
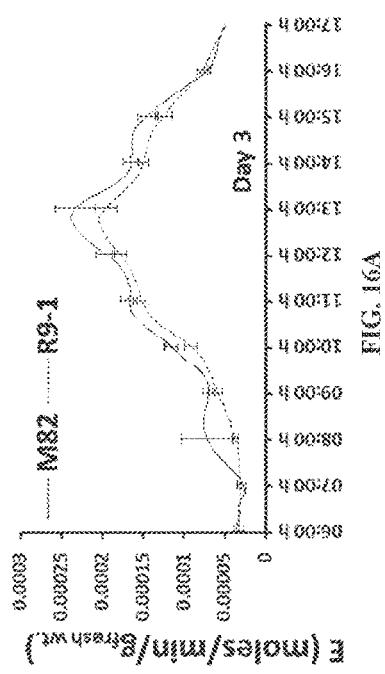
FIGS. 16C and 16D: Correlation between E and VPD at time of VPD increase between 08:30 to 11:30 (from low till the time of high reached peak of E during the midday in FIGS. 16A and 16B, respectively) during days 3 and day 5, respectively.
Figure 16D:
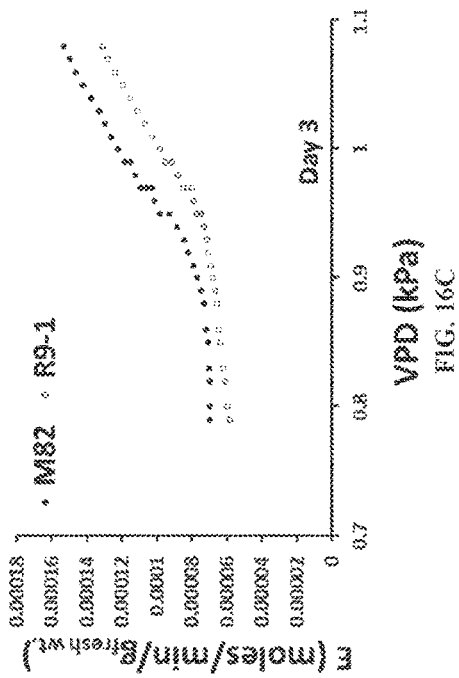
Figure 16E:
FIG. 16E: Tomato plants during the experiment in a semi-controlled glasshouse.

The differences between M82 and line r9-1 in whole plant transpiration rate (E) were examined using continuous measurements for 5 days under well irrigation conditions in a semi-controlled greenhouse (FIG. 16E). The system continuous and momentary measurements allowed to analyze E throughout the day from sunrise (06:00 hours) to sunset (17:00 hours) and thus track down the whole plant response to increase in VPD that takes place from early morning and peaks at midday (FIG. 14A). In accordance with the results obtained at the cell and tissue and organ levels, the whole plant transpiration of r9-1 plants was significantly lower than M82 during the midday hours (FIG. 14B). Remarkably, the difference in E between the lines were most visible during midday hours (FIGS. 14B, C and D; gray background, FIGS. 15B-G and 16A and 16B) while no differences in transpiration rate were seen at early morning or evening hours (FIGS. 14C and D). Moreover, the analysis revealed differences in the response of the whole plant E to daily rise in VPD as represented by E to VPD plots (FIGS. 14E and F). Thus, it seems that rop9-1 plants are able to normally allow $H_2O$ and $CO_2$ diffusion at early morning hours before the large surge in VPD (i.e., increase in water loss), while maintaining relative lower E at conditions of increased water loss. This behavior can explain the higher WUE of the rop9 mutants as compared to M82 and the ability of rop9 mutants to maintain similar shoot weight and yield component as M82 under well irrigation conditions (FIG. 16E and FIG. 5). Overall, these results describe the continuous response of the plant to changes in diurnal changes in radiation and temperatures. During early hours (from sunrise at 6 AM to 8 AM) and in the afternoon and early evening (between 3 PM and 5 PM) the transpiration of the rop9 mutant and M82 is the same. However, in mid-day between (9 AM and 2 PM) at which time the VPD is high, the transpiration of the rop9 mutant is lower. VPD is the force that drives the water vapor transpiration from the plants and depends on the air humidity and the temperature. There is a direct relation between the VPD and transpiration; the higher the transpiration the higher the VPD. The results show that Water Use Efficiency (WUE) of the rop9 mutant is improved. The advantage is that one could use less water for irrigating the plants, a highly desired goal given the global warming and the shortages in fresh water.

Example 7: ABA Effects on ROP Function in Guard Cells

To follow the regulation of ROP activity in guard cells a fluorescent probe which is specifically expressed in guard cells was generated. The probe consists GFP fused to the 173 C-terminal residues of ROP effector ICR1 (between residues 171-344) and was designated GFP-ICRΔN. Our previous studies demonstrated that ICR1 is recruited to the plasma membrane by active ROPs (Lavy M, et al. Curr Biol 17, 947-952. 2007), and that the C-terminal domain between residues 171-344, which lacks the N-terminal microtubules binding domain, interacts with ROPs as strong as the full-length protein. To prevent possible steric hindrance of the ICRΔN moiety by GFP, a flexible linker consisting of 3 repeats of $(Gly)_4Ser$ (3×GGGGS) sequence were cloned between the ICRΔN and the GFP moieties. To prevent negative effects that could occur due to long-term expression of a ROP effector, the expression of the probe was induced by estradiol under regulation of the ROP11 promoter. In *Arabidopsis* leaves/cotyledons, this resulted in inducible and reproducible expression of the ICRΔN-GFP probe specifically in guard cells (not shown). The distribution of the probe between the membrane and cytoplasm reflected the degree of ROP activation. One-hour treatments with 10 μM ABA resulted in significant shift of the probe from the plasma membrane to the cytoplasm and the results were reproducible in independent experiments that were carried with two independent transgenic *Arabidopsis* lines. These guard-cell specific results obtained with the ICRΔN-GFP confirmed earlier findings which were obtained by biochemical precipitations of GST-PAK, a mammalian Rac effector (Lemichez E, et al. Genes Dev 15, 1808-1816. 2001). Yet, the function of ROP in guard cells and the effect of its inactivation on plants WUE is shown for the first time in the present invention.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A plant or a part thereof comprising at least one cell modified to have reduced expression and/or activity of SlROP9 protein or of an ortholog thereof comprising an amino acid sequence at least 90% identical to the amino acid sequence set forth in SEQ ID NO:1 compared to an unmodified cell, wherein the modified cell comprises within its genome at least one mutant allele of SlROP9 or of an ortholog thereof encoding a mutant protein or a mutant ortholog thereof comprising at least one mutation in at least one protein domain selected from the group consisting of G-domain, hypervariable domain and a combination thereof, wherein the plant has enhanced water use efficiency (WUE) compared to a control plant grown under the same conditions.

2. The plant of claim 1, wherein said plant has enhanced tolerance to drought and/or salt stress.

3. The plant of claim 1, wherein the SlROP9 protein or the ortholog is encoded by SlROP9 gene having at least 80% identity to the nucleic acid sequence set forth in SEQ ID NO:2.

4. The plant of claim 1, wherein the Slrop9 mutant allele comprises a nucleic acid sequence selected from the group consisting of SEQ ID NO:3 (rop-9-1), SEQ ID NO:4 (rop-9-2), SEQ ID NO:5 (rop-9-3), and SEQ ID NO:6 (rop-9-4), encoding SlROP9 mutant protein comprising an amino acid sequence selected from the group consisting of SEQ ID NO:7 (ROP-9-1), SEQ ID NO:8 (ROP-9-2), SEQ ID NO:9 (ROP-9-3), and SEQ ID NO:10 (ROP-9-4).

5. The plant of claim 1, wherein the mutation is a site-specific mutation inserted by a gene-editing method using at least one artificially engineered nuclease.

6. A plant or a part thereof comprising at least one cell modified to have reduced expression and/or activity of SlROP9 protein or of an ortholog thereof comprising an amino acid sequence at least 90% identical to the amino acid sequence set forth in SEQ ID NO: 1 compared to an unmodified cell, wherein said plant is a transgenic plant, and wherein the at least one cell modified to have reduced expression and/or activity of SlROP9 protein or an ortholog thereof comprises at least one silencing molecule targeted to SlROP9 or to an ortholog thereof.

7. The plant of claim 1, wherein the WUE of said plant is at least 10% higher compared to the WUE of the control plant under irrigation conditions.

8. The plant of claim 2, wherein said plant, when exposed to drought or salt stress conditions, shows at least 10% reduction in symptoms of leaf wilting compared to leaf wilting symptoms of the control plant under same drought or salt stress conditions.

9. The plant of claim 1, wherein said plant is selected from the group consisting of a field crop plant, a cereal plant, an ornamental plant, a forest tree and a forest shrub.

10. A seed of the plant of claim 1, wherein a plant grown from the seed comprises at least one cell modified to have reduced expression and/or activity of SlROP9 protein or of an ortholog thereof comprising an amino acid sequence at least 90% identical to the amino acid sequence set forth in SEQ ID NO:1 compared to an unmodified cell, wherein the modified cell comprises within its genome at least one mutant allele of SlROP9 or of an ortholog thereof encoding a mutant protein or a mutant ortholog thereof comprising at least one mutation in at least one protein domain selected from the group consisting of G-domain, hypervariable domain and a combination thereof, and wherein the plant has enhanced water use efficiency compared to a control plant grown under the same conditions.

11. A tissue culture comprising at least one modified cell of the plant of claim 1 or a protoplast derived therefrom, wherein a plant regenerated from the tissue culture comprises at least one cell modified to have reduced expression and/or activity of SlROP9 protein or of an ortholog thereof comprising an amino acid sequence at least 90% identical to the amino acid sequence set forth in SEQ ID NO:1 compared to an unmodified cell, wherein the modified cell comprises within its genome at least one mutant allele of SlROP9 or of an ortholog thereof encoding a mutant protein or a mutant ortholog thereof comprising at least one mutation in at least one protein domain selected from the group consisting of G-domain, hypervariable domain and a combination thereof, and wherein the plant has enhanced water use efficiency compared to a control plant grown under the same conditions.

12. A method for producing a plant with enhanced water use efficiency, the method comprising reducing the expression and/or activity of SlROP9 protein or an ortholog thereof comprising an amino acid sequence at least 90% identical to the amino acid sequence set forth in SEQ ID NO:1 within at least one cell of the plant, wherein the method comprises introducing at least one mutation in at least one allele of SlROP9 gene or an ortholog thereof encoding the SlROP9 protein or ortholog thereof, and wherein the at least one mutation results in an encoded protein having at least one mutation in at least one protein domain selected from the group consisting of G-domain, hypervariable domain and a combination thereof.

13. The method of claim 12, wherein the SlROP9 protein or the ortholog thereof is encoded by SlROP9 gene having at least 80% identity to the nucleic acid sequence set forth in SEQ ID NO:2.

14. The method of claim 12, wherein said method comprises inducing the mutation by genome editing using at least one artificially engineered nuclease.

15. A method for producing a plant with enhanced water use efficiency, the method comprising reducing the expression and/or activity of SlROP9 protein or of an ortholog thereof comprising an amino acid sequence at least 90% identical to the amino acid sequence set forth in SEQ ID NO: 1 within at least one cell, said method comprises transforming the at least one cell with at least one SlROP9-silencing molecule targeted to an endogenous gene encoding the SlROP9 or an ortholog thereof, thereby producing a transgenic plant.

16. The method of claim 12, wherein the expression and/or activity of the SlROP9 protein or the ortholog thereof is reduced by at least 60%, compared to the expression of SlROP9 in a corresponding unmodified cell.

17. The method of claim 12, wherein the plant produced is characterized by an enhanced tolerance to drought or salt stress compared to a corresponding wild type plant having unmodified expression of SlROP9.

18. The plant of claim 6, wherein the WUE of said plant is at least 10% higher compared to the WUE of the control plant under irrigation conditions.

19. The method of claim 15, wherein the expression and/or activity of the SlROP9 protein or the ortholog thereof is reduced by at least 60%, compared to the expression of SlROP9 in a corresponding unmodified cell.

20. The method of claim 15, wherein the plant produced is characterized by an enhanced tolerance to drought or salt stress compared to a corresponding wild type plant having unmodified expression of SlROP9.

\* \* \* \* \*

SEQUENCE LISTING

```
<160> NUMBER OF SEQ ID NOS: 53

<210> SEQ ID NO 1
<211> LENGTH: 210
<212> TYPE: PRT
<213> ORGANISM: Solanum lycopersicum

<400> SEQUENCE: 1

Met Ala Ser Ser Ala Ser Arg Phe Ile Lys Cys Val Thr Val Gly Asp
1               5                   10                  15

Gly Ala Val Gly Lys Thr Cys Met Leu Ile Cys Tyr Thr Ser Asn Lys
            20                  25                  30

Phe Pro Thr Asp Tyr Val Pro Thr Val Phe Asp Asn Phe Ser Ala Asn
        35                  40                  45

Val Val Val Glu Gly Thr Thr Val Asn Leu Gly Leu Trp Asp Thr Ala
    50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Val Ser Arg Ala Ser Tyr Glu
                85                  90                  95

Asn Ile Leu Lys Lys Trp Ile Pro Glu Leu Gln His Tyr Ala Pro Gly
            100                 105                 110

Ile Pro Val Val Leu Ala Gly Thr Lys Leu Asp Leu Arg Glu Asp Lys
        115                 120                 125

His Phe Leu Ala Asp His Pro Gly Leu Val Pro Val Thr Thr Ala Gln
    130                 135                 140

Gly Glu Glu Leu Arg Lys Gln Ile Gly Ala Ala Tyr Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Lys Pro Pro Gln Lys Gln Lys Glu Lys Lys Lys Gln
            180                 185                 190

Arg Arg Gly Cys Leu Met Asn Val Met Cys Gly Arg Lys Leu Val Cys
        195                 200                 205

Leu Lys
    210

<210> SEQ ID NO 2
<211> LENGTH: 633
<212> TYPE: DNA
<213> ORGANISM: Solanum lycopersicum

<400> SEQUENCE: 2
atggcctcaa gtgcttcaag attcatcaaa tgtgtcacgg ttggtgatgg ggctgttggc      60
aagacttgta tgcttatttg ctataccagt aacaagtttc ccactgacta tgttccgacg     120
gtgtttgaca acttcagcgc caatgtggtt gttgaaggga ccacagtaaa tttaggtctt     180
tgggatactg caggacaaga agattataac agattaaggc cactgagcta ccgaggagca     240
gatgtttttg tcctagcgtt ctccttggtg agtcgtgcaa gctatgaaaa catacttaag     300
```

```
aagtggattc ccgaacttca gcattatgct cctggaattc cggtggtatt agctggcacc    360
aaacttgatc ttcgtgagga taagcacttc ttggctgatc atcctggatt agttcctgtc    420
accactgcgc agggagagga gctgcggaaa caaattggtg ctgcctatta tatcgaatgt    480
agctctaaaa cacaacagaa tgtgaaagct gtatttgatg ctgcaatcaa ggtcgtcatc    540
aagccaccac aaaagcaaaa ggagaagaaa aacaacgtc ggggatgtct catgaatgtg    600
atgtgcggaa ggaagctcgt tgttttaaag tga                                 633
```

<210> SEQ ID NO 3
<211> LENGTH: 373
<212> TYPE: DNA
<213> ORGANISM: Artificial Sequence
<220> FEATURE:
<223> OTHER INFORMATION: SlROP9 Mutant
<220> FEATURE:
<221> NAME/KEY: misc_feature
<223> OTHER INFORMATION: Synthetic

<400> SEQUENCE: 3

```
taggagtggg ggtgggggag aaacttaccc taaggaaaat gaaatggtca cctaatcaac     60
tttggggaat gttagtagct cagtatggtt aactgaactt tcacattgtt ggtgaattgt    120
tggtgagggt ttgattccac accttggaat cccctcccca cttttccctt ttaaaaaaag    180
accgtatcag ctagaaagaa cagaatgtta tggttaactc gtgtgattca ggagtatttg    240
ttgagtttct ttcctgagct tgaacttcag ttttctgagt ggttgtatat gttcaaacca    300
ggatctatgt tccaacggtg tttgacaact tcagcgccaa tgtgggtgtt aagggaccca    360
cagtaaattt agg                                                       373
```

<210> SEQ ID NO 4
<211> LENGTH: 360
<212> TYPE: DNA
<213> ORGANISM: Artificial Sequence
<220> FEATURE:
<223> OTHER INFORMATION: SlROP9 Mutant
<220> FEATURE:
<221> NAME/KEY: misc_feature
<223> OTHER INFORMATION: Synthetic

<400> SEQUENCE: 4

```
gggggtgggg gagaaactta ccctaaggaa aatgaaatgg tcacctaatc aactttgggg     60
aatgttagta gctcagtatg gttaactgaa ctttcacatt gttggtgaat gttggtgag    120 ggtttgattc cacaccttgg aatcccctcc ccacttttcc cttttaaaaa aagaccgtat    180
cagctagaaa gaacagaatg ttatggttaa ctcgtgtgat tcaggagtat tgttgagtt    240 tctttcctga gcttgaactt cagttttctg agtggttgta tatgttcaaa ccaggattcc    300
aacggtgttt gacaacttca gcgccaatgt ggttgttgaa gggaccacag taaatttagg    360
```

<210> SEQ ID NO 5
<211> LENGTH: 506
<212> TYPE: DNA
<213> ORGANISM: Artificial Sequence
<220> FEATURE:
<223> OTHER INFORMATION: SlROP9 Mutant
<220> FEATURE:
<221> NAME/KEY: misc_feature
<223> OTHER INFORMATION: Synthetic

<400> SEQUENCE: 5

```
ggcgttctcc ttggtgagtg gggcaagcta tgaaaacata cttaagaagg tatttctgtt      60
gaaaacagtg aactttgtga gtttgtatca tatgtattta agattgctaa aatcccattt     120
ttggtcagtg gattcccgaa cttcagcatt atgctcctgg aaccggtggt attagctggc     180
accaaacttg gtaagtattt aacatgttcc ctgaagctaa gttataacaa atgctgattc     240
ttgaatgtaa ctgcttcagt ttaatgtcac tttgttctat gatgtgcttg ctaaaatgct     300
aatatgtcta cttataaaaa ataaatataa aatgttgatg tgttgaatgt agctgtactt     360
tgtagttttc agagtttatt gtcgctaata ctgtattcaa aagcgtaaat aacttaaggg     420
gattgcacga tggaggtaaa aagacgtgaa tacagtataa cttaaggaga ttgcatgacc     480
ggagggaggt ctagagatgg aactgg                                          506
```

<210> SEQ ID NO 6
<211> LENGTH: 762
<212> TYPE: DNA
<213> ORGANISM: Artificial Sequence
<220> FEATURE:
<223> OTHER INFORMATION: SlROP9 Mutant
<220> FEATURE:
<221> NAME/KEY: misc_feature
<223> OTHER INFORMATION: Synthetic

<400> SEQUENCE: 6

```
atggcctcaa gtgcttcaag attcatcaaa tgtgtcacgg ttggtgatgg ggctgttggc      60
aagacttgta tgcttatttg ctataccagt aacaagtttc ccactgacta tgttccgacg     120
gtgtttgaca acttcagcgc caatgtggtt gttgaaggga ccacagtaaa tttaggtctt     180
tgggatactg caggacaaga agattataac agattaaggc cactgagcta ccgaggagca     240
gatgtttttg tcctagcgtt ctccttggtg agtcgtgcaa gctatgaaaa catacttaag     300
aaggtatttc tgttgaaaac agtgaacttt gtgagtttgt atcatatgta tttaagattg     360
ctaaaatccc attttggtc agtggattcc cgaacttcag cattatgctc ctggattccg     420
gtggtattag ctggcaccaa acttggtaag tatttaacat gttccctgaa gctaagttat     480
aacaaatgct gattcttgaa tgtaactgct tcagtttaat gtcactttgt tctatgatgt     540
gcttgctaaa atgctaatat gtctacttat aaaaataaa tataaaatgt tgatgtgttg     600
aatgtagctg tactttgtag ttttcagagt ttattgtcgc taatactgta ttcaaaagcg     660
taaataactt aaggggattg cacgatggag gtaaaaagac gtgaatacag tataacttaa     720
ggagattgca tgaccggagg gaggtctaga gatggaactg ga                        762
```

<210> SEQ ID NO 7
<211> LENGTH: 42
<212> TYPE: PRT
<213> ORGANISM: Artificial Sequence
<220> FEATURE:
<223> OTHER INFORMATION: SlROP9 Mutant
<220> FEATURE:
<221> NAME/KEY: misc_feature
<223> OTHER INFORMATION: Synthetic

<400> SEQUENCE: 7

```
Met Ala Ser Ser Ala Ser Arg Phe Ile Lys Cys Val Thr Val Gly Asp
1               5                   10                  15

Gly Ala Val Gly Lys Thr Cys Met Leu Ile Cys Tyr Thr Ser Asn Lys
            20                  25                  30
```

Phe Pro Thr Asp Leu Cys Ser Asp Gly Val
        35                  40

<210> SEQ ID NO 8
<211> LENGTH: 40
<212> TYPE: PRT
<213> ORGANISM: Artificial Sequence
<220> FEATURE:
<223> OTHER INFORMATION: S1ROP9 Mutant
<220> FEATURE:
<221> NAME/KEY: misc_feature
<223> OTHER INFORMATION: Synthetic

<400> SEQUENCE: 8

Met Ala Ser Ser Ala Ser Arg Phe Ile Lys Cys Val Thr Val Gly Asp
1               5                   10                  15

Gly Ala Val Gly Lys Thr Cys Met Leu Ile Cys Tyr Thr Ser Asn Lys
            20                  25                  30

Phe Pro Thr Asp Ser Asp Gly Val
        35                  40

<210> SEQ ID NO 9
<211> LENGTH: 121
<212> TYPE: PRT
<213> ORGANISM: Artificial Sequence
<220> FEATURE:
<223> OTHER INFORMATION: S1ROP9 Mutant
<220> FEATURE:
<221> NAME/KEY: misc_feature
<223> OTHER INFORMATION: Synthetic

<400> SEQUENCE: 9

Met Ala Ser Ser Ala Ser Arg Phe Ile Lys Cys Val Thr Val Gly Asp
1               5                   10                  15

Gly Ala Val Gly Lys Thr Cys Met Leu Ile Cys Tyr Thr Ser Asn Lys
            20                  25                  30

Phe Pro Thr Asp Tyr Val Pro Thr Val Phe Asp Asn Phe Ser Ala Asn
        35                  40                  45

Val Val Val Glu Gly Thr Thr Val Asn Leu Gly Leu Trp Asp Thr Ala
    50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Val Ser Arg Ala Ser Tyr Glu
                85                  90                  95

Asn Ile Leu Lys Lys Trp Ile Pro Glu Leu Gln His Tyr Ala Pro Gly
            100                 105                 110

Thr Gly Gly Ile Ser Trp His Gln Thr
        115                 120

<210> SEQ ID NO 10
<211> LENGTH: 116
<212> TYPE: PRT
<213> ORGANISM: Artificial Sequence
<220> FEATURE:
<223> OTHER INFORMATION: S1ROP9 Mutant
<220> FEATURE:
<221> NAME/KEY: misc_feature
<223> OTHER INFORMATION: Synthetic

<400> SEQUENCE: 10

Met Ala Ser Ser Ala Ser Arg Phe Ile Lys Cys Val Thr Val Gly Asp
1               5                   10                  15

```
Gly Ala Val Gly Lys Thr Cys Met Leu Ile Cys Tyr Thr Ser Asn Lys
            20                  25                  30

Phe Pro Thr Asp Tyr Val Pro Thr Val Phe Asp Asn Phe Ser Ala Asn
        35                  40                  45

Val Val Val Glu Gly Thr Thr Val Asn Leu Gly Leu Trp Asp Thr Ala
 50                  55                  60

Gly Gln Glu Asp Tyr Asn Arg Leu Arg Pro Leu Ser Tyr Arg Gly Ala
 65                  70                  75                  80

Asp Val Phe Val Leu Ala Phe Ser Leu Val Ser Arg Ala Ser Tyr Glu
                85                  90                  95

Asn Ile Leu Lys Lys Trp Ile Pro Glu Leu Gln His Tyr Ala Pro Gly
            100                 105                 110

Phe Arg Trp Tyr
        115

<210> SEQ ID NO 11
<211> LENGTH: 373
<212> TYPE: DNA
<213> ORGANISM: Artificial Sequence
<220> FEATURE:
<223> OTHER INFORMATION: SlROP9 Variant
<220> FEATURE:
<221> NAME/KEY: misc_feature
<223> OTHER INFORMATION: Synthetic

<400> SEQUENCE: 11
gtaggagtgg gggtggggga gaaacttacc ctaaggaaaa tgaaatggtc acctaatcaa    60
ctttggggaa tgttagtagc tcagtatggt taactgaact ttcacattgt tggtgaattg   120
ttggtgaggg tttgattcca caccttggaa tcccctcccc acttttccct tttaaaaaaa   180
gaccgtatca gctagaaaga acagaatgtt atggttaact cgtgtgattc aggagtattt   240
gttgagtttc tttcctgagc ttgaacttca gttttctgag tggttgtata tgttcaaacc   300
aggactatgt tccaacggtg tttgacaact tcagcgccaa tgtggttgtt gaagggacca   360
cagtaaattt agg                                                     373

<210> SEQ ID NO 12
<211> LENGTH: 506
<212> TYPE: DNA
<213> ORGANISM: Artificial Sequence
<220> FEATURE:
<223> OTHER INFORMATION: SlROP9 Variant
<220> FEATURE:
<221> NAME/KEY: misc_feature
<223> OTHER INFORMATION: Synthetic
<220> FEATURE:
<221> NAME/KEY: misc_feature
<222> LOCATION: (7)..(7)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u

<400> SEQUENCE: 12
gttctcnttg gtgantgcgt gcaagctatg aaaacatact taagaaggta tttctgttga    60
aaacagtgaa ctttgtgagt ttgtatcata tgtatttaag attgctaaaa tcccattttt   120
ggtcagtgga ttcccgaact tcagcattat gctcctggaa ttccggtggt attagctggc   180
accaaacttg gtaagtattt aacatgttcc ctgaagctaa gttataacaa atgctgattc   240 tgaatgtaa ctgcttcagt ttaatgtcac tttgttctat gatgtgcttg ctaaaatgct   300
```

```
aatatgtcta cttataaaaa ataaatataa aatgttgatg tgttgaatgt agctgtactt    360
tgtagttttc agagtttatt gtcgctaata ctgtattcaa aagcgtaaat aacttaaggg    420
gattgcacga tggaggtaaa aagacgtgaa tacagtataa cttaaggaga ttgcatgacc    480
ggagggaggt ctagagatgg aactgg                                         506
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide - Primer

<400> SEQUENCE: 13
cacattggtc aggccggtat                                                20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide - Primer

<400> SEQUENCE: 14
atctggccat caggctgaat                                                20

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligonucleotide - Primer

<400> SEQUENCE: 15
gtgtcacggt tggtgatggg g                                              21

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide - Primer

<400> SEQUENCE: 16
ctgctcctcg gtagctcagt gg                                             22

<210> SEQ ID NO 17
<211> LENGTH: 51
<212> TYPE: DNA
<213> ORGANISM: Artificial Sequence
<220> FEATURE:
<223> OTHER INFORMATION: Synthetic Oligonucleotide - Primer

<400> SEQUENCE: 17
ggggacagct ttcttgtaca aagtggccgc ctcaagtgct tcaagattca t             51

<210> SEQ ID NO 18
<211> LENGTH: 55
<212> TYPE: DNA
<213> ORGANISM: Artificial Sequence
<220> FEATURE:
<223> OTHER INFORMATION: Synthetic Oligonucleotide - Primer
```

<400> SEQUENCE: 18 ggggacaaact ttgtataata aagttgttca ctttaaacaa acgagcttcc ttccg    55

<210> SEQ ID NO 19
<211> LENGTH: 67
<212> TYPE: DNA
<213> ORGANISM: Artificial Sequence
<220> FEATURE:
<223> OTHER INFORMATION: Synthetic Oligonucleotide - Primer

<400> SEQUENCE: 19
ggggacaagt ttgtacaaaa aagcaggctt aatgccaaga ttaaggggat cagatatgct    60
tcaaagg    67

<210> SEQ ID NO 20
<211> LENGTH: 63
<212> TYPE: DNA
<213> ORGANISM: Artificial Sequence
<220> FEATURE:
<223> OTHER INFORMATION: Synthetic Oligonucleotide - Primer

<400> SEQUENCE: 20
gggaccactt tgtacaagaa agctgggtgt tgtgtccct tctttctcca caggtatcca    60
agc    63

<210> SEQ ID NO 21
<211> LENGTH: 60
<212> TYPE: DNA
<213> ORGANISM: Artificial Sequence
<220> FEATURE:
<223> OTHER INFORMATION: Synthetic Oligonucleotide - Primer

<400> SEQUENCE: 21
ggggacaagt ttgtacaaaa aagcaggctt aatgccaaga tcaaggggat cagaaatgcc    60

<210> SEQ ID NO 22
<211> LENGTH: 60
<212> TYPE: DNA
<213> ORGANISM: Artificial Sequence
<220> FEATURE:
<223> OTHER INFORMATION: Synthetic Oligonucleotide - Primer

<400> SEQUENCE: 22
ggggaccact tgtacaaga aagctgggtg tttgtggccc ttcttcttcc agaggtcacc    60

<210> SEQ ID NO 23
<211> LENGTH: 56
<212> TYPE: DNA
<213> ORGANISM: Artificial Sequence
<220> FEATURE:
<223> OTHER INFORMATION: Synthetic Oligonucleotide - Primer

<400> SEQUENCE: 23
tgtggtctca attgcaccgt cggaacatag tccgttttag agctagaaat agcaag    56

<210> SEQ ID NO 24
<211> LENGTH: 56
<212> TYPE: DNA
<213> ORGANISM: Artificial Sequence
<220> FEATURE:
<223> OTHER INFORMATION: Synthetic Oligonucleotide - Primer

```
<400> SEQUENCE: 24
tgtggtctca attgctaata ccaccggaat tccgttttag agctagaaat agcaag        56

<210> SEQ ID NO 25
<211> LENGTH: 31
<212> TYPE: DNA
<213> ORGANISM: Artificial Sequence
<220> FEATURE:
<223> OTHER INFORMATION: Synthetic Oligonucleotide - Primer

<400> SEQUENCE: 25
tgtggtctca agcgtaatgc caactttgta c                                    31

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide - Primer

<400> SEQUENCE: 26
gatccatgaa cccagctgac gg                                              22

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide - Primer

<400> SEQUENCE: 27
ctacctgagc acccagtccg                                                 20

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide - Primer

<400> SEQUENCE: 28
gtcgccgtcc agctcgac                                                   18

<210> SEQ ID NO 29
<211> LENGTH: 21
<212> TYPE: DNA
<213> ORGANISM: Artificial Sequence
<220> FEATURE:
<223> OTHER INFORMATION: Synthetic Oligonucleotide - Primer

<400> SEQUENCE: 29
cgggggaggc agagggtttc c                                               21

<210> SEQ ID NO 30
<211> LENGTH: 56
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (15)..(33)
<223> OTHER INFORMATION: n is a, c, g, t or u
```

-continued

<400> SEQUENCE: 30
tgtggtctca attgnnnnnn nnnnnnnnnn nnngttttag agctagaaat agcaag      56

<210> SEQ ID NO 31
<211> LENGTH: 210
<212> TYPE: PRT
<213> ORGANISM: Solanum pennellii

<400> SEQUENCE: 31

Met Ala Ser Ser Ala Ser Arg Phe Ile Lys Cys Val Thr Val Gly Asp
1               5                   10                  15

Gly Ala Val Gly Lys Thr Cys Met Leu Ile Cys Tyr Thr Ser Asn Lys
            20                  25                  30

Phe Pro Thr Asp Tyr Val Pro Thr Val Phe Asp Asn Phe Ser Ala Asn
        35                  40                  45

Val Val Val Glu Gly Thr Thr Val Asn Leu Gly Leu Trp Asp Thr Ala
    50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Val Ser Arg Ala Ser Tyr Glu
                85                  90                  95

Asn Ile Leu Lys Lys Trp Ile Pro Glu Leu Gln His Tyr Ala Pro Gly
            100                 105                 110

Ile Pro Val Val Leu Ala Gly Thr Lys Leu Asp Leu Arg Glu Asp Lys
        115                 120                 125

His Phe Leu Ala Asp His Pro Gly Leu Val Pro Val Thr Thr Ala Gln
    130                 135                 140

Gly Glu Glu Leu Arg Lys Gln Ile Gly Ala Ala Tyr Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Lys Pro Pro Gln Lys Gln Lys Glu Lys Lys Lys Gln
            180                 185                 190

Arg Arg Gly Cys Leu Met Asn Val Met Cys Gly Arg Lys Leu Val Cys
        195                 200                 205

Leu Lys
    210

<210> SEQ ID NO 32
<211> LENGTH: 210
<212> TYPE: PRT
<213> ORGANISM: Solanum melongena

<400> SEQUENCE: 32

Met Ala Ser Ser Ala Ser Arg Phe Ile Lys Cys Val Thr Val Gly Asp
1               5                   10                  15

Gly Ala Val Gly Lys Thr Cys Met Leu Ile Cys Tyr Thr Ser Asn Lys
            20                  25                  30

Phe Pro Thr Asp Tyr Val Pro Thr Val Phe Asp Asn Phe Ser Ala Asn
        35                  40                  45

Val Val Val Glu Gly Thr Thr Val Asn Leu Gly Leu Trp Asp Thr Ala
    50                  55                  60

Gly Gln Glu Asp Tyr Asn Arg Leu Arg Pro Leu Ser Tyr Arg Gly Ala
65                  70                  75                  80

```
Asp Val Phe Val Leu Ala Phe Ser Leu Val Ser Arg Ala Ser Tyr Glu
                85                  90                  95

Asn Ile Leu Lys Lys Trp Ile Pro Glu Leu Gln His Tyr Ala Pro Gly
            100                 105                 110

Ile Pro Val Val Leu Ala Gly Thr Lys Leu Asp Leu Arg Glu Asp Lys
        115                 120                 125

His Phe Leu Ala Asp His Pro Gly Leu Val Pro Val Thr Thr Ala Gln
    130                 135                 140

Gly Glu Glu Leu Arg Lys Gln Ile Gly Ala Ala Tyr Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Lys Pro Pro Gln Lys Gln Lys Glu Lys Lys Lys Gln
            180                 185                 190

His Arg Gly Cys Leu Met Asn Val Met Cys Gly Arg Lys Leu Val Cys
        195                 200                 205

Leu Lys
    210

<210> SEQ ID NO 33
<211> LENGTH: 208
<212> TYPE: PRT
<213> ORGANISM: Arabidopsis thaliana

<400> SEQUENCE: 33

Met Ala Ser Ser Ala Ser Lys Phe Ile Lys Cys Val Thr Val Gly Asp
1               5                   10                  15

Gly Ala Val Gly Lys Thr Cys Met Leu Ile Cys Tyr Thr Ser Asn Lys
            20                  25                  30

Phe Pro Thr Asp Tyr Ile Pro Thr Val Phe Asp Asn Phe Ser Val Asn
        35                  40                  45

Val Val Val Glu Gly Ile Thr Val Asn Leu Gly Leu Trp Asp Thr Ala
    50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Ile Ser Arg Ala Ser Tyr Glu
                85                  90                  95

Asn Val Phe Lys Lys Trp Ile Pro Glu Leu Gln His Phe Ala Pro Gly
            100                 105                 110

Val Pro Ile Val Leu Val Gly Thr Lys Met Asp Leu Arg Glu Asp Arg
        115                 120                 125

His Tyr Leu Ser Asp His Pro Gly Leu Ser Pro Val Thr Thr Ser Gln
    130                 135                 140

Gly Glu Glu Leu Arg Lys His Ile Gly Ala Thr Tyr Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Lys Pro Ala Val Lys Gln Lys Glu Lys Lys Lys Lys
            180                 185                 190

Gln Lys Pro Arg Ser Gly Cys Leu Ser Asn Ile Leu Cys Gly Lys Asn
        195                 200                 205

<210> SEQ ID NO 34
<211> LENGTH: 215
<212> TYPE: PRT
```

<213> ORGANISM: Arabidopsis thaliana

<400> SEQUENCE: 34

```
Met Ala Ser Ala Ser Lys Phe Ile Lys Cys Val Thr Val Gly Asp
1               5                   10                  15
Gly Ala Val Gly Lys Thr Cys Met Leu Ile Cys Tyr Thr Ser Asn Lys
            20                  25                  30
Phe Pro Thr Asp Tyr Ile Pro Thr Val Phe Asp Asn Phe Ser Ala Asn
            35                  40                  45
Val Val Val Glu Gly Thr Thr Val Asn Leu Gly Leu Trp Asp Thr Ala
    50                  55                  60
Gly Gln Glu Asp Tyr Asn Arg Leu Arg Pro Leu Ser Tyr Arg Gly Ala
65                  70                  75                  80
Asp Val Phe Val Leu Ser Phe Ser Leu Val Ser Arg Ala Ser Tyr Glu
                85                  90                  95
Asn Val Phe Lys Lys Trp Ile Pro Glu Leu Gln His Phe Ala Pro Gly
            100                 105                 110
Val Pro Leu Val Leu Val Gly Thr Lys Leu Asp Leu Arg Glu Asp Lys
            115                 120                 125
His Tyr Leu Ala Asp His Pro Gly Leu Ser Pro Val Thr Thr Ala Gln
    130                 135                 140
Gly Glu Glu Leu Arg Lys Leu Ile Gly Ala Thr Tyr Tyr Ile Glu Cys
145                 150                 155                 160
Ser Ser Lys Thr Gln Gln Asn Val Lys Ala Val Phe Asp Ser Ala Ile
                165                 170                 175
Lys Glu Val Ile Lys Pro Leu Val Lys Gln Lys Glu Lys Thr Lys Lys
            180                 185                 190
Lys Lys Lys Gln Lys Ser Asn His Gly Cys Leu Ser Asn Val Leu Cys
            195                 200                 205
Gly Arg Ile Val Thr Arg His
    210                 215
```

<210> SEQ ID NO 35
<211> LENGTH: 99
<212> TYPE: DNA
<213> ORGANISM: Artificial Sequence
<220> FEATURE:
<223> OTHER INFORMATION: SlROP9-1 Mutant Partial Sequence
<220> FEATURE:
<221> NAME/KEY: misc_feature
<223> OTHER INFORMATION: Synthetic

<400> SEQUENCE: 35
gttttctgag tggttgtata tgttcaaacc aggatctatg ttccaacggt gtttgacaac    60
ttcagcgcca atgtggttgt tgaagggacc acagtaaat                            99

<210> SEQ ID NO 36
<211> LENGTH: 92
<212> TYPE: DNA
<213> ORGANISM: Artificial Sequence
<220> FEATURE:
<223> OTHER INFORMATION: SlROP9-2 Mutant Partial Sequence
<220> FEATURE:
<221> NAME/KEY: misc_feature
<223> OTHER INFORMATION: Synthetic

<400> SEQUENCE: 36
gttttctgag tggttgtata tgttcaaacc aggattccaa cggtgtttga caacttcagc    60
gccaatgtgg ttgttgaagg gaccacagta aa                                   92

<210> SEQ ID NO 37
<211> LENGTH: 75
<212> TYPE: DNA
<213> ORGANISM: Artificial Sequence
<220> FEATURE:
<223> OTHER INFORMATION: SlROP9 Partial Sequence
<220> FEATURE:
<221> NAME/KEY: misc_feature
<223> OTHER INFORMATION: Synthetic

<400> SEQUENCE: 37

```
gttttctgag tggttgtata tgttcaaacc aggactatgt tccaacggtg tttgacaact    60
tcagcgccaa tgtgg                                                     75
```

<210> SEQ ID NO 38
<211> LENGTH: 73
<212> TYPE: DNA
<213> ORGANISM: Artificial Sequence
<220> FEATURE:
<223> OTHER INFORMATION: SlROP9 Partial Sequence
<220> FEATURE:
<221> NAME/KEY: misc_feature
<223> OTHER INFORMATION: Synthetic

<400> SEQUENCE: 38

```
gtggattccc gaacttcagc attatgctcc tggaattccg gtggtattag ctggcaccaa    60
acttggtaag tat                                                       73
```

<210> SEQ ID NO 39
<211> LENGTH: 71
<212> TYPE: DNA
<213> ORGANISM: Artificial Sequence
<220> FEATURE:
<223> OTHER INFORMATION: SlROP9-3 Mutant Partial Sequence
<220> FEATURE:
<221> NAME/KEY: misc_feature
<223> OTHER INFORMATION: Synthetic

<400> SEQUENCE: 39

```
gtggattccc gaacttcagc attatgctcc tggaaccggt ggtattagct ggcaccaaac    60
ttggtaagta t                                                         71
```

<210> SEQ ID NO 40
<211> LENGTH: 72
<212> TYPE: DNA
<213> ORGANISM: Artificial Sequence
<220> FEATURE:
<223> OTHER INFORMATION: SlROP9-4 Mutant Partial Sequence
<220> FEATURE:
<221> NAME/KEY: misc_feature
<223> OTHER INFORMATION: Synthetic

<400> SEQUENCE: 40

```
gtggattccc gaacttcagc attatgctcc tggattccgg tggtattagc tggcaccaaa    60
cttggtaagt at                                                        72
```

<210> SEQ ID NO 41
<211> LENGTH: 100
<212> TYPE: PRT
<213> ORGANISM: Artificial Sequence
<220> FEATURE:
<223> OTHER INFORMATION: SlROP9 Partial Sequence
<220> FEATURE:
<221> NAME/KEY: misc_feature
<223> OTHER INFORMATION: Synthetic

```
<400> SEQUENCE: 41

Asn Lys Phe Pro Thr Asp Tyr Val Pro Thr Val Phe Asp Asn Phe Ser
1               5                   10                  15

Ala Asn Val Val Val Glu Gly Thr Thr Val Asn Leu Gly Leu Trp Asp
            20                  25                  30

Thr Ala Gly Gln Glu Asp Tyr Asn Arg Leu Arg Pro Leu Ser Tyr Arg
        35                  40                  45

Gly Ala Asp Val Phe Val Leu Ala Phe Ser Leu Val Ser Arg Ala Ser
    50                  55                  60

Tyr Glu Asn Ile Leu Lys Lys Trp Ile Pro Glu Leu Gln His Tyr Ala
65                  70                  75                  80

Pro Gly Ile Pro Val Val Leu Ala Gly Thr Lys Leu Asp Leu Arg Glu
                85                  90                  95

Asp Lys His Phe
            100

<210> SEQ ID NO 42
<211> LENGTH: 12
<212> TYPE: PRT
<213> ORGANISM: Artificial Sequence
<220> FEATURE:
<223> OTHER INFORMATION: SlROP9-2 Mutant Partial Sequence
<220> FEATURE:
<221> NAME/KEY: misc_feature
<223> OTHER INFORMATION: Synthetic

<400> SEQUENCE: 42

Asn Lys Phe Pro Thr Asp Leu Cys Ser Asp Gly Val
1               5                   10

<210> SEQ ID NO 43
<211> LENGTH: 10
<212> TYPE: PRT
<213> ORGANISM: Artificial Sequence
<220> FEATURE:
<223> OTHER INFORMATION: SlROP9-2 Mutant Partial Sequence
<220> FEATURE:
<221> NAME/KEY: misc_feature
<223> OTHER INFORMATION: Synthetic

<400> SEQUENCE: 43

Asn Lys Phe Pro Thr Asp Ser Asp Gly Val
1               5                   10

<210> SEQ ID NO 44
<211> LENGTH: 91
<212> TYPE: PRT
<213> ORGANISM: Artificial Sequence
<220> FEATURE:
<223> OTHER INFORMATION: SlROP9-3 Mutant Partial Sequence
<220> FEATURE:
<221> NAME/KEY: misc_feature
<223> OTHER INFORMATION: Synthetic

<400> SEQUENCE: 44

Asn Lys Phe Pro Thr Asp Tyr Val Pro Thr Val Phe Asp Asn Phe Ser
1               5                   10                  15

Ala Asn Val Val Val Glu Gly Thr Thr Val Asn Leu Gly Leu Trp Asp
            20                  25                  30

Thr Ala Gly Gln Glu Asp Tyr Asn Arg Leu Arg Pro Leu Ser Tyr Arg
        35                  40                  45
```

Gly Ala Asp Val Phe Val Leu Ala Phe Ser Leu Val Ser Arg Ala Ser
            50                  55                  60

Tyr Glu Asn Ile Leu Lys Lys Trp Ile Pro Glu Leu Gln His Tyr Ala
65                  70                  75                  80

Pro Gly Thr Gly Gly Ile Ser Trp His Gln Thr
                85                  90

<210> SEQ ID NO 45
<211> LENGTH: 86
<212> TYPE: PRT
<213> ORGANISM: Artificial Sequence
<220> FEATURE:
<223> OTHER INFORMATION: SlROP9-4 Mutant Partial Sequence
<220> FEATURE:
<221> NAME/KEY: misc_feature
<223> OTHER INFORMATION: Synthetic

<400> SEQUENCE: 45

Asn Lys Phe Pro Thr Asp Tyr Val Pro Thr Val Phe Asp Asn Phe Ser
1               5                   10                  15

Ala Asn Val Val Val Glu Gly Thr Thr Val Asn Leu Gly Leu Trp Asp
            20                  25                  30

Thr Ala Gly Gln Glu Asp Tyr Asn Arg Leu Arg Pro Leu Ser Tyr Arg
        35                  40                  45

Gly Ala Asp Val Phe Val Leu Ala Phe Ser Leu Val Ser Arg Ala Ser
    50                  55                  60

Tyr Glu Asn Ile Leu Lys Lys Trp Ile Pro Glu Leu Gln His Tyr Ala
65                  70                  75                  80

Pro Gly Phe Arg Trp Tyr
                85

<210> SEQ ID NO 46
<211> LENGTH: 46
<212> TYPE: DNA
<213> ORGANISM: Artificial Sequence
<220> FEATURE:
<223> OTHER INFORMATION: SlROP9 Partial Sequence
<220> FEATURE:
<221> NAME/KEY: misc_feature
<223> OTHER INFORMATION: Synthetic

<400> SEQUENCE: 46
gtatatgttc aaaccaggac tatgttccaa cggtgtttga caactt                46

<210> SEQ ID NO 47
<211> LENGTH: 47
<212> TYPE: DNA
<213> ORGANISM: Artificial Sequence
<220> FEATURE:
<223> OTHER INFORMATION: SlROP9-1 Mutant Partial Sequence
<220> FEATURE:
<221> NAME/KEY: misc_feature
<223> OTHER INFORMATION: Synthetic

<400> SEQUENCE: 47
gtatatgttc aaaccaggat ctatgttcca acggtgtttg acaactt               47

<210> SEQ ID NO 48
<211> LENGTH: 50
<212> TYPE: DNA
<213> ORGANISM: Artificial Sequence
<220> FEATURE:
<223> OTHER INFORMATION: SlROP9 Partial Sequence
<220> FEATURE:

<221> NAME/KEY: misc_feature
<223> OTHER INFORMATION: Synthetic

<400> SEQUENCE: 48
tgtatatgtt caaaccagga ctatgttcca acggtgtttg acaacttcag         50

<210> SEQ ID NO 49
<211> LENGTH: 45
<212> TYPE: DNA
<213> ORGANISM: Artificial Sequence
<220> FEATURE:
<223> OTHER INFORMATION: SlROP9-3 Mutant Partial Sequence
<220> FEATURE:
<221> NAME/KEY: misc_feature
<223> OTHER INFORMATION: Synthetic

<400> SEQUENCE: 49
tgtatatgtt caaaccagga ttccaacggt gtttgacaac ttcag              45

<210> SEQ ID NO 50
<211> LENGTH: 47
<212> TYPE: DNA
<213> ORGANISM: Artificial Sequence
<220> FEATURE:
<223> OTHER INFORMATION: SlROP9 Partial Sequence
<220> FEATURE:
<221> NAME/KEY: misc_feature
<223> OTHER INFORMATION: Synthetic

<400> SEQUENCE: 50
cgaacttcag cattatgctc ctggaattcc ggtggtatta gctggca            47

<210> SEQ ID NO 51
<211> LENGTH: 45
<212> TYPE: DNA
<213> ORGANISM: Artificial Sequence
<220> FEATURE:
<223> OTHER INFORMATION: SlROP9-2 Mutant Partial Sequence
<220> FEATURE:
<221> NAME/KEY: misc_feature
<223> OTHER INFORMATION: Synthetic

<400> SEQUENCE: 51
cgaacttcag cattatgctc ctggaaccgg tggtattagc tggca              45

<210> SEQ ID NO 52
<211> LENGTH: 47
<212> TYPE: DNA
<213> ORGANISM: Artificial Sequence
<220> FEATURE:
<223> OTHER INFORMATION: SlROP9 Partial Sequence
<220> FEATURE:
<221> NAME/KEY: misc_feature
<223> OTHER INFORMATION: Synthetic

<400> SEQUENCE: 52
gaacttcagc attatgctcc tggaattccg gtggtattag ctggcac            47

<210> SEQ ID NO 53
<211> LENGTH: 46
<212> TYPE: DNA
<213> ORGANISM: Artificial Sequence
<220> FEATURE:
<223> OTHER INFORMATION: SlROP9-4 Mutant Partial Sequence
<220> FEATURE:
<221> NAME/KEY: misc_feature
<223> OTHER INFORMATION: Synthetic

```
<400> SEQUENCE: 53
gaacttcagc attatgctcc tggattccgg tggtattagc tggcac                46
```